(12) United States Patent
Michihata et al.

(10) Patent No.: US 10,485,629 B2
(45) Date of Patent: Nov. 26, 2019

(54) ENDOSCOPE DEVICE

(71) Applicant: Sony Olympus Medical Solutions Inc., Tokyo (JP)

(72) Inventors: Taihei Michihata, Kanagawa (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 71 days.

(21) Appl. No.: 15/893,796

(22) Filed: Feb. 12, 2018

(65) Prior Publication Data
US 2018/0243043 A1   Aug. 30, 2018

(30) Foreign Application Priority Data

Feb. 24, 2017  (JP) ................................. 2017-033934
Feb. 24, 2017  (JP) ................................. 2017-033935

(51) Int. Cl.
    *A61B 90/00*  (2016.01)
    *H04N 7/18*   (2006.01)
    (Continued)

(52) U.S. Cl.
CPC .......... *A61B 90/06* (2016.02); *A61B 1/00009* (2013.01); *A61B 1/00018* (2013.01); *A61B 1/00045* (2013.01); *A61B 1/00087* (2013.01); *A61B 1/00105* (2013.01); *A61B 1/00188* (2013.01); *A61B 1/042* (2013.01); *A61B 1/045* (2013.01); *A61B 1/05* (2013.01); *A61B 1/07* (2013.01); *G06T 7/50* (2017.01); *G06T 7/571* (2017.01); *H04N 5/2256* (2013.01); *H04N 5/2351* (2013.01); *H04N 5/2353* (2013.01); *H04N 5/2354* (2013.01); *H04N 5/243* (2013.01); *H04N 7/183* (2013.01);
(Continued)

(58) Field of Classification Search
CPC ............ A61B 1/00009; A61B 1/00018; A61B 1/00045; A61B 1/00087; A61B 1/00105; A61B 1/00188; A61B 1/042; A61B 1/045; A61B 1/05; A61B 1/07; A61B 2090/061; A61B 90/06; G06T 2207/10068; G06T 7/50; G06T 7/571; H04N 2005/2255; H04N 5/2256; H04N 5/2351; H04N 5/2353; H04N 5/2354; H04N 5/243; H04N 7/183
See application file for complete search history.

(56) References Cited

U.S. PATENT DOCUMENTS 3,730,632 A * 5/1973 Chikama ............ A61B 1/00165
                                            356/636
5,054,491 A * 10/1991 Saito .................... A61B 1/0005
                                            600/109
(Continued)

FOREIGN PATENT DOCUMENTS

JP         2015-134039         7/2015

*Primary Examiner* — Peter D Le
(74) *Attorney, Agent, or Firm* — Xsensus LLP

(57) ABSTRACT

An endoscope device includes: an insertion unit configured to be inserted into a subject and capture a subject image inside the subject from a distal end thereof; an imaging unit configured to capture the subject image; a subject distance calculation unit configured to calculate a subject distance between the distal end of the insertion unit and the subject; and a distance information notification unit configured to give a notice of distance information on the subject distance.

14 Claims, 19 Drawing Sheets

(51) Int. Cl.
*H04N 5/225* (2006.01)
*A61B 1/05* (2006.01)
*A61B 1/00* (2006.01)
*H04N 5/235* (2006.01)
*H04N 5/243* (2006.01)
*G06T 7/50* (2017.01)
*A61B 1/045* (2006.01)
*A61B 1/04* (2006.01)
*A61B 1/07* (2006.01)
*G06T 7/571* (2017.01)

(52) U.S. Cl.
CPC .......... *A61B 2090/061* (2016.02); *G06T 2207/10068* (2013.01); *H04N 2005/2255* (2013.01)

(56) References Cited

U.S. PATENT DOCUMENTS

| | | | | |
|---|---|---|---|---|
| 5,436,655 A * | 7/1995 | Hiyama | A61B 1/00193 348/139 |
| 5,573,492 A * | 11/1996 | Dianna | A61B 5/1076 356/4.03 |
| 5,617,858 A * | 4/1997 | Taverna | A61B 1/00154 600/407 |
| 2002/0137986 A1* | 9/2002 | Ogawa | A61B 1/0005 600/160 |
| 2005/0228221 A1* | 10/2005 | Hirakawa | A61B 1/00009 600/101 |
| 2006/0025692 A1* | 2/2006 | Ishihara | A61B 1/00096 600/478 |
| 2007/0185384 A1* | 8/2007 | Bayer | A61B 1/00174 600/129 |
| 2008/0154129 A1* | 6/2008 | Mizunuma | A61B 90/39 600/431 |
| 2009/0086017 A1* | 4/2009 | Miyano | G02B 23/243 348/65 |
| 2009/0216077 A1* | 8/2009 | Banju | A61B 1/018 600/103 |
| 2009/0292166 A1* | 11/2009 | Ito | A61B 1/00009 600/109 |
| 2012/0053408 A1* | 3/2012 | Miyamoto | G06T 7/74 600/109 |
| 2015/0054929 A1* | 2/2015 | Ito | A61B 1/273 348/65 |
| 2016/0274350 A1* | 9/2016 | Aizenfeld | G02B 23/2438 |
| 2016/0310043 A1* | 10/2016 | Levi | A61B 5/1076 |

* cited by examiner

ENDOSCOPE DEVICE

CROSS-REFERENCE TO RELATED APPLICATION(S)

The present application claims priority to and incorporates by reference the entire contents of Japanese Patent Application No. 2017-033934 filed in Japan on Feb. 24, 2017 and Japanese Patent Application No. 2017-033935 filed in Japan on Feb. 24, 2017.

BACKGROUND

The present disclosure relates to an endoscope device.

In the medical field and the industrial field, endoscope devices for observing inside a subject, such as a human or a mechanical structure, have been known (for example, refer to Japanese Laid-open Patent Publication No. 2015-134039).

An endoscope device described in Japanese Laid-open Patent Publication No. 2015-134039 includes: an insertion unit that is inserted into a subject and captures a subject image inside the subject from a distal end thereof; an imaging unit (imaging element) that captures the subject image and outputs an image signal; a control device that processes the image signal and generates a video signal for displaying; and a display device that displays an image based on the video signal.

SUMMARY

An endoscope device according to one aspect of the present disclosure may include: an insertion unit configured to be inserted into a subject and capture a subject image inside the subject from a distal end thereof; an imaging unit configured to capture the subject image; a subject distance calculation unit configured to calculate a subject distance between the distal end of the insertion unit and the subject; and a distance information notification unit configured to give a notice of distance information on the subject distance.

DETAILED DESCRIPTION

Embodiments will be described below with reference to the drawings. The present disclosure is not limited by the embodiments described below. The same components are denoted by the same reference signs in illustration of the drawings.

First Embodiment

Schematic Configuration of Endoscope Device

Figure 1:
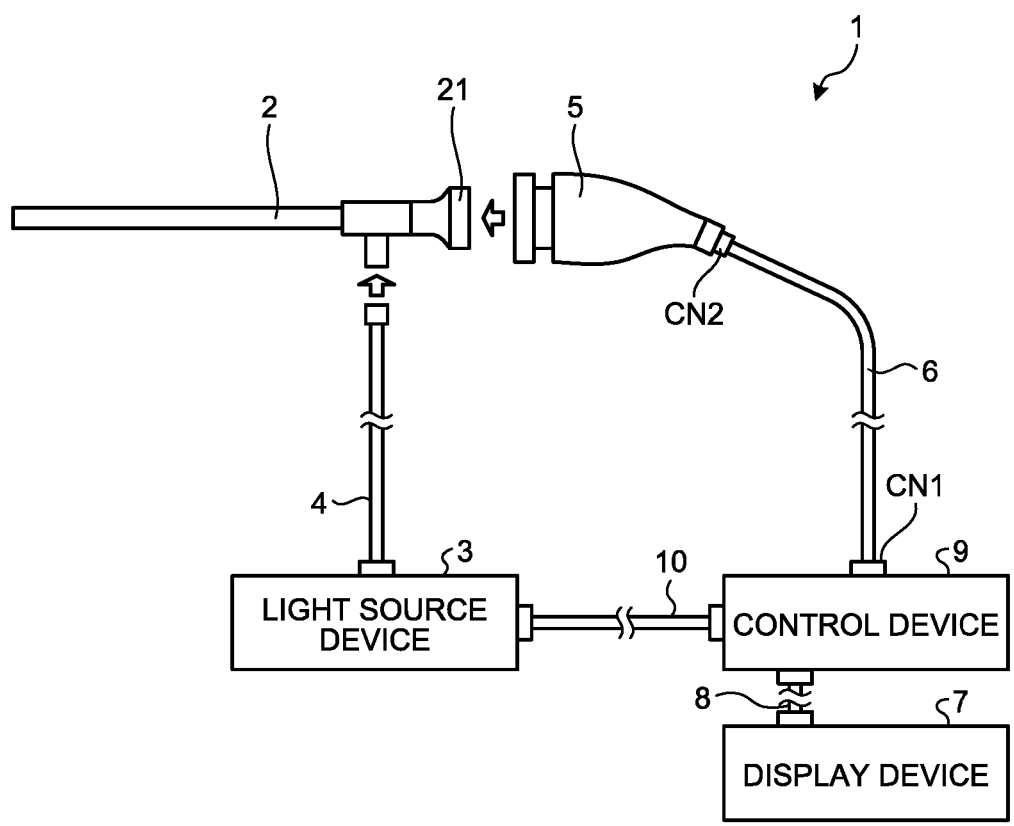
FIG. 1 is a diagram illustrating a schematic configuration of an endoscope device according to a first embodiment.

FIG. 1 is a diagram illustrating a schematic configuration of an endoscope device 1 according to a first embodiment.

The endoscope device 1 is a device that is used in the medical field for observing inside a living body. As illustrated in FIG. 1, the endoscope device 1 includes an insertion unit 2, a light source device 3, a light guide 4, a camera head 5, a first transmission cable 6, a display device 7, a second transmission cable 8, a control device 9, and a third transmission cable 10.

The insertion unit 2 is configured with a rigid endoscope. Specifically, the insertion unit 2 is rigid or at least partially flexible, has an elongated shape, and is inserted into a living body. An optical system, which is configured using one or more lenses and collects light from a subject image, is provided inside the insertion unit 2.

One end of the light guide 4 is connected to the light source device 3, and the light source device 3 supplies light for illuminating inside a living body to the one end of the light guide 4 under the control of the control device 9.

The one end of the light guide 4 is connected to the light source device 3 in a freely attachable and detachable manner, and the other end of the light guide 4 is connected to the insertion unit 2 in a freely attachable and detachable manner. The light guide 4 transmits light supplied from the light source device 3 from the one end thereof to the other end thereof to supply the light to the insertion unit 2. The light supplied to the insertion unit 2 is emitted from a distal end of the insertion unit 2, and emitted into the living body. The light emitted into the living body and reflected inside the living body (subject image) is collected by the optical system in the insertion unit 2.

The camera head 5 is connected to a proximal end (an eyepiece portion 21 (FIG. 1)) of the insertion unit 2 in a freely attachable and detachable manner. Under the control of the control device 9, the camera head 5 captures the subject image condensed by the insertion unit 2, and outputs an image signal (RAW signal) resulting from the imaging. The image signal is, for example, an image signal of 4K or higher.

A detailed configuration of the camera head 5 will be described later.

The first transmission cable 6 has one end that is connected to the control device 9 via a connector CN1 (FIG. 1) in a freely attachable and detachable manner, and another end that is connected to the camera head 5 via a connector CN2 (FIG. 1) in a freely attachable and detachable manner. The first transmission cable 6 transmits image signals and the like, which are output from the camera head 5, to the control device 9, and also transmits control signals, synchronization signals, a clock, electrical power, and the like, which are output from the control device 9, to the camera head 5.

Regarding the transmission of image signals, etc. from the camera head 5 to the control device 9 via the first transmission cable 6, the image signals, etc. may be transmitted either as optical signals or as electrical signals. The same applies to the transmission of control signals, synchronization signals, and a clock from the control device 9 to the camera head 5 via the first transmission cable 6.

Under the control of the control device 9, the display device 7 displays a display image based on a video signal output from the control device 9, and outputs sound according to a control signal output from the control device 9. The display device 7 includes a display unit 71 and a sound output unit 72 (see FIG. 2).

The display unit 71 is configured using a display, such as a liquid crystal display or an organic electroluminescence (EL) display, and displays a display image based on a video signal output from the control device 9.

The sound output unit 72 is configured using a speaker or the like, and outputs, as sound, distance information on a subject distance between the distal end of the insertion unit 2 and a subject in accordance with a control signal output from the control device 9.

The second transmission cable 8 has one end that is connected to the display device 7 in a freely attachable and detachable manner, and another end that is connected to the control device 9 in a freely attachable and detachable manner. The second transmission cable 8 transmits a video signal processed by the control device 9 and a control signal output from the control device 9 to the display device 7.

The control device 9 is configured to include a central processing unit (CPU) or the like, and comprehensively controls operation of the light source device 3, the camera head 5, and the display device 7.

A detailed configuration of the control device 9 will be described later.

The third transmission cable 10 has one end that is connected to the light source device 3 in a freely attachable and detachable manner, and another end that is connected to the control device 9 in a freely attachable and detachable manner. The third transmission cable 10 transmits a control signal output from the control device 9 to the light source device 3.

Configuration of Camera Head

Next, a configuration of the camera head 5 will be described.

Figure 2:
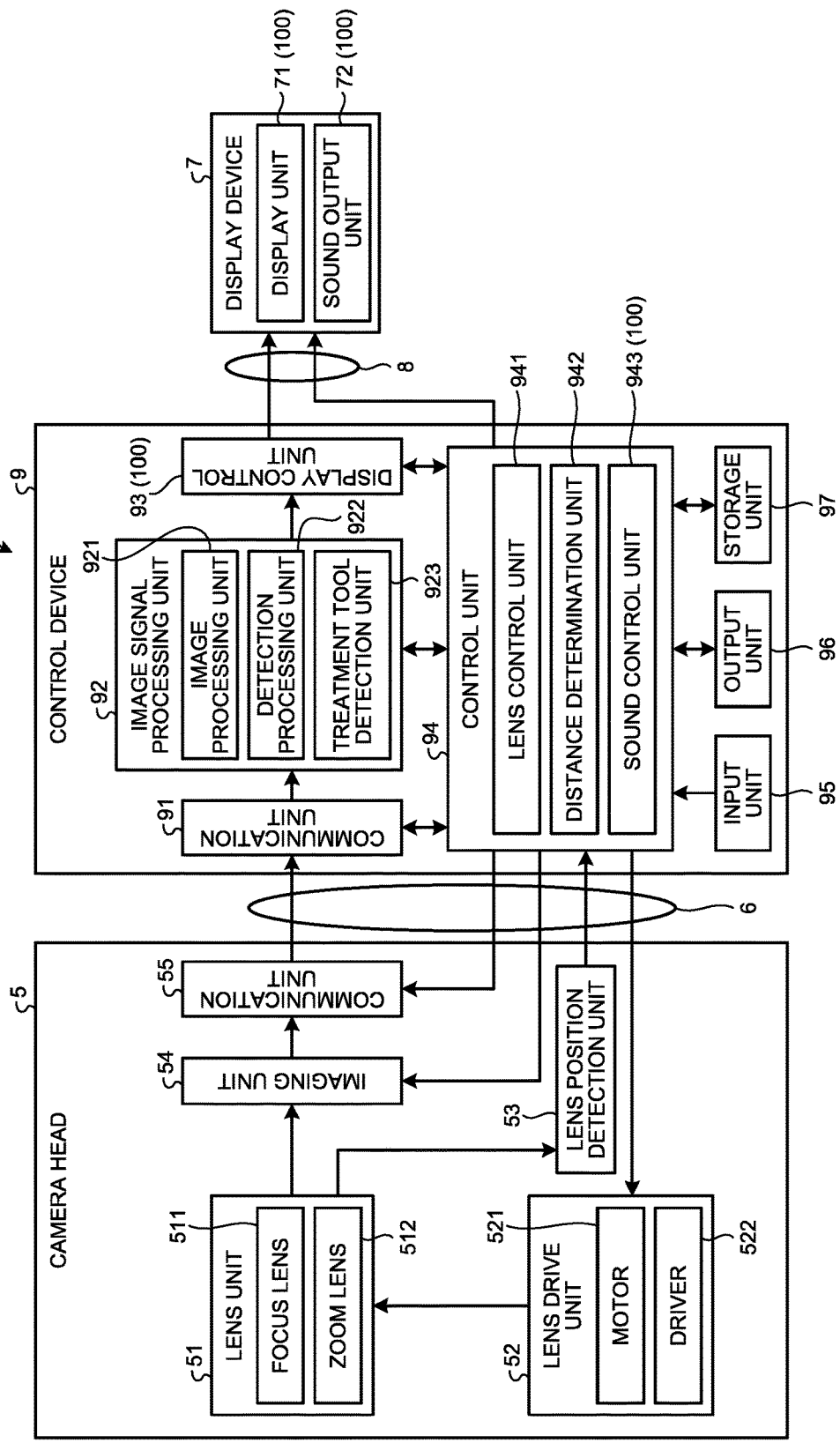
FIG. 2 is a block diagram illustrating configurations of a camera head and a control device.

FIG. 2 is a block diagram illustrating configurations of the camera head 5 and the control device 9.

In FIG. 2, for convenience of explanation, illustration of the connectors CN1 and CN2 between the control device 9, the camera head 5, and the first transmission cable 6, and illustration of connectors between the control device 9, the display device 7, and the second transmission cable 8 are omitted.

As illustrated in FIG. 2, the camera head 5 includes a lens unit 51, a lens drive unit 52, a lens position detection unit 53, an imaging unit 54, and a communication unit 55.

The lens unit 51 is configured using a plurality of lenses that are movable along an optical axis, and forms a subject image condensed by the insertion unit 2 onto an imaging plane of the imaging unit 54. As illustrated in FIG. 2, the lens unit 51 includes a focus lens 511 and a zoom lens 512.

The focus lens 511 is configured using one or more lenses, and moves along an optical axis to adjust a focal point.

The zoom lens 512 is configured using one or more lenses, and moves along the optical axis to adjust an angle of view. The zoom lens 512 has a function as an image enlargement unit.

The lens unit 51 further includes a focus mechanism (not illustrated) that moves the focus lens 511 along the optical axis, and an optical zoom mechanism (not illustrated) that moves the zoom lens 512 along the optical axis.

As illustrated in FIG. 2, the lens drive unit 52 includes a motor 521 that operates the focus mechanism and the optical zoom mechanism described above, and a driver 522 that drives the motor 521. The lens drive unit 52 adjusts the focal point and the angle of view of the lens unit 51 under the control of the control device 9.

The lens position detection unit 53 has a function as a subject distance calculation unit that calculates a subject distance between the distal end of the insertion unit 2 and a subject. The lens position detection unit 53 is configured using a position sensor, such as a photo interrupter, and detects a lens position of the focus lens 511 (hereinafter, described as a focus position) and a lens position of the zoom lens 512 (hereinafter, described as a zoom position). The lens position detection unit 53 outputs a detection signal corresponding to the focus position and the zoom position to the control device 9 via the first transmission cable 6.

In the first embodiment, when the focus lens 511 is positioned at a near point, the lens position detection unit 53 detects "0" as the focus position. When the focus lens 511 is positioned at a far point, the lens position detection unit 53 detects "100" as the focus position. That is, the focus lens 511 is movable in a range of "0" to "100".

The imaging unit 54 captures an image inside a living body under the control of the control device 9. The imaging unit 54 is configured using a sensor chip, in which an imaging element (not illustrated) such as a charge coupled device (CCD) or a complementary metal oxide semiconductor (CMOS) that receives a subject image condensed by the insertion unit 2 and formed by the lens unit 51 and converts the subject image to an electrical signal, a signal processing unit (not illustrated) that performs signal processing (A/D conversion or the like) on the electrical signal (analog signal) output from the imaging element and outputs an image signal, and the like are integrally formed. The imaging unit 54 outputs the image signal (digital image) obtained by the A/D conversion. The signal processing unit (not illustrated) described above may be separately provided rather than integrated with the imaging element.

The communication unit 55 functions as a transmitter that transmits image signals output from the imaging unit 54 to the control device 9 via the first transmission cable 6. The communication unit 55 is configured with a high-speed serial interface that communicates image signals with the control device 9 via the first transmission cable 6 at a transmission rate of 1 Gbps or higher, for example.

Configuration of Control Device

Next, a configuration of the control device 9 will be described with reference to FIG. 2.

As illustrated in FIG. 2, the control device 9 includes a communication unit 91, an image signal processing unit 92, a display control unit 93, a control unit 94, an input unit 95, an output unit 96, and a storage unit 97.

The communication unit 91 functions as a receiver that receives image signals output from the camera head 5 (the communication unit 55) via the first transmission cable 6. The communication unit 91 is configured with a high-speed serial interface that communicates image signals with the communication unit 55 at a transmission rate of 1 Gbps or higher, for example.

The image signal processing unit 92 processes image signals (RAW signals) that are output from the camera head 5 (the communication unit 55) and received by the communication unit 91, under the control of the control unit 94. As illustrated in FIG. 2, the image signal processing unit 92 includes an image processing unit 921, a detection processing unit 922, and a treatment tool detection unit 923.

The image processing unit 921 performs RAW processing, such as optical black subtraction processing or demosaicing, on an image signal (RAW signal) received by the communication unit 91, and converts the RAW signal (image signal) to an RGB signal (image signal). The image processing unit 921 further performs RGB processing, such as white balancing, RGB gamma correction, or YC conversion (conversion from an RGB signal to a luminance signal and a color difference signal (Y, $C_B/C_R$ signals)), on the RGB signal (image signal). The image processing unit 921 further performs YC processing, such as color difference correction or noise reduction, on the Y, $C_B/C_R$ signals (image signals).

The detection processing unit 922 performs detection processing for controlling the camera head 5 (autofocus (AF) processing or the like) on the image signals (Y, $C_B/C_R$ signals) processed by the image processing unit 921.

For example, based on pixel information (luminance signal (Y signal)) on each of pixels in a predetermined area (hereinafter, described as a detection area) in the whole image of one frame captured by the imaging unit 54, the detection processing unit 922 detects contrast or frequency components of an image in the detection area. The detection processing unit 922 outputs detection information (contrast or frequency components) obtained by the detection to the control unit 94.

The treatment tool detection unit 923 performs treatment tool detection processing for detecting a used state of a treatment tool, such as an electric scalpel, that is inserted into a living body.

Figure 3:
FIG. 3 is a diagram for explaining treatment tool detection processing performed by a treatment tool detection unit.
Figure 4:
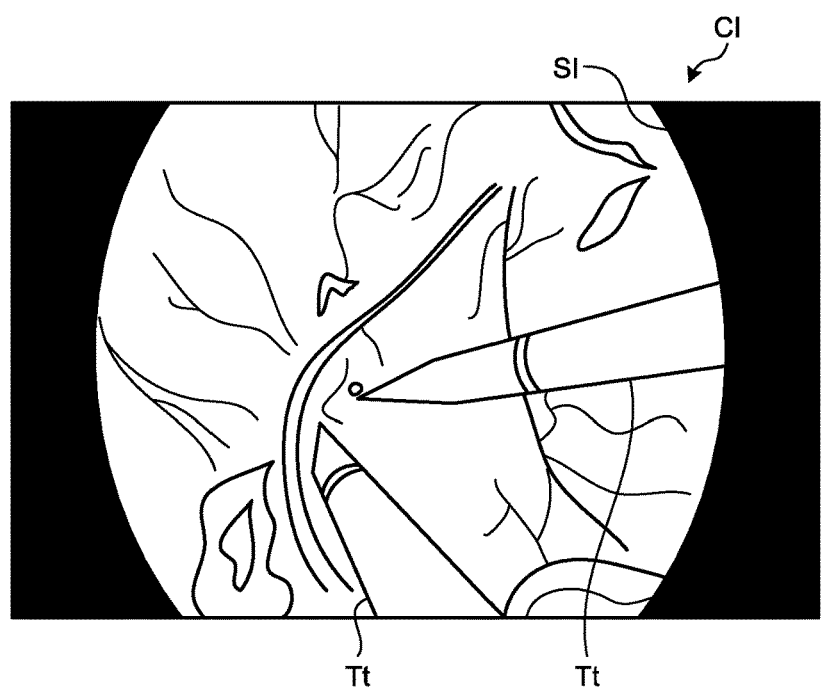
FIG. 4 is a diagram for explaining the treatment tool detection processing performed by the treatment tool detection unit.

FIG. 3 and FIG. 4 are diagrams for explaining the treatment tool detection processing performed by the treatment tool detection unit 923.

In the first embodiment, the treatment tool detection unit 923 determines whether a treatment tool Tt is included in a subject image SI inside a captured image CI that is based on image signals processed by the image processing unit 921, by using a well-known method, such as pattern matching, for example. If it is determined that the treatment tool Tt is not included in the subject image SI inside the captured image CI (FIG. 3), the treatment tool detection unit 923 outputs a detection signal, which indicates that the treatment tool Tt is not used, to the control unit 94. In contrast, if it is determined that the treatment tool Tt is included in the subject image SI inside the captured image CI (FIG. 4), the treatment tool detection unit 923 outputs a detection signal, which indicates that the treatment tool Tt is used, to the control unit 94.

The display control unit 93 generates a video signal, which is used for displaying and in which distance information on the subject distance between the distal end of the insertion unit 2 and a subject is superimposed on the captured image CI that is based on the image signals (Y, $C_B/C_R$ signals) processed by the image processing unit 921, by performing on-screen display (OSD) processing or the like under the control of the control unit 94. The display control unit 93 outputs the video signal to the display device 7 (the display unit 71) via the second transmission cable 8.

The control unit 94 is configured using, for example, a CPU or the like, and outputs control signals via the first to third transmission cables 6, 8, and 10 to control operation of the light source device 3, the camera head 5, and the display device 7, and operation of the whole control device 9. As illustrated in FIG. 2, the control unit 94 includes a lens control unit 941, a distance determination unit 942, and a sound control unit 943.

The lens control unit 941 operates the lens drive unit 52 and adjusts the focal point or the angle of view (changes the focus position or the zoom position) of the lens unit 51. For example, the lens control unit 941 performs AF processing based on the focus position detected by the lens position detection unit 53 and the detection information output by the detection processing unit 922 as will described below.

Figure 5:
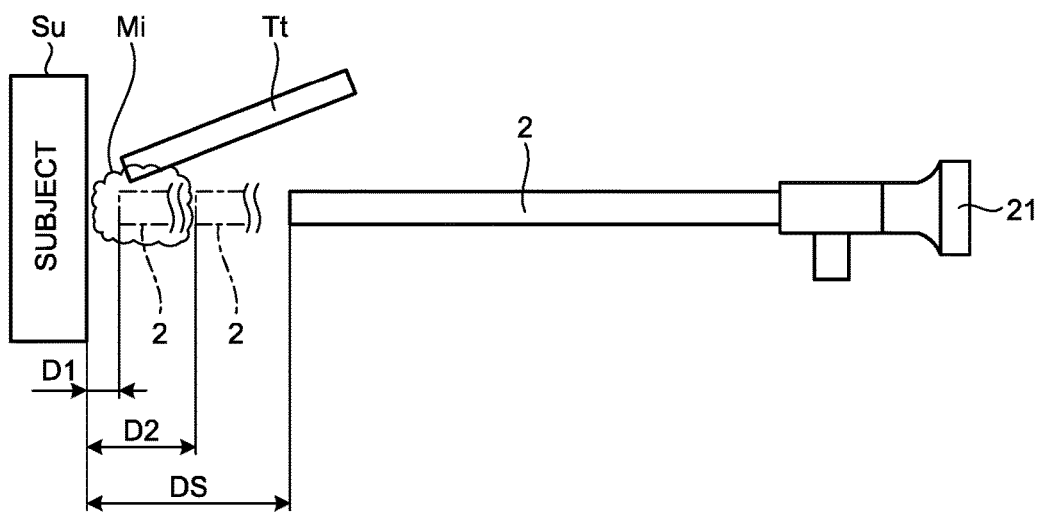
FIG. 5 is a diagram for explaining AF processing performed by a lens control unit.
Figure 6:
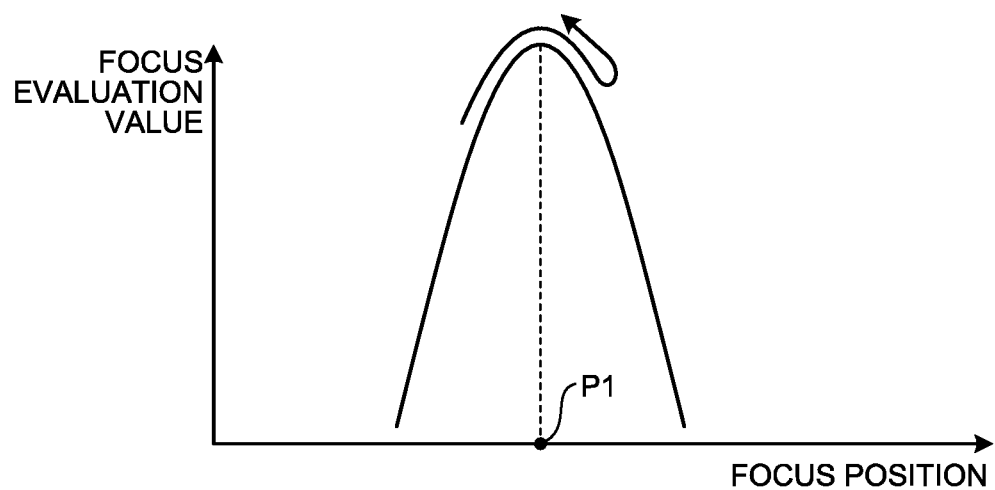
FIG. 6 is a diagram for explaining AF processing performed by the lens control unit.
Figure 7:
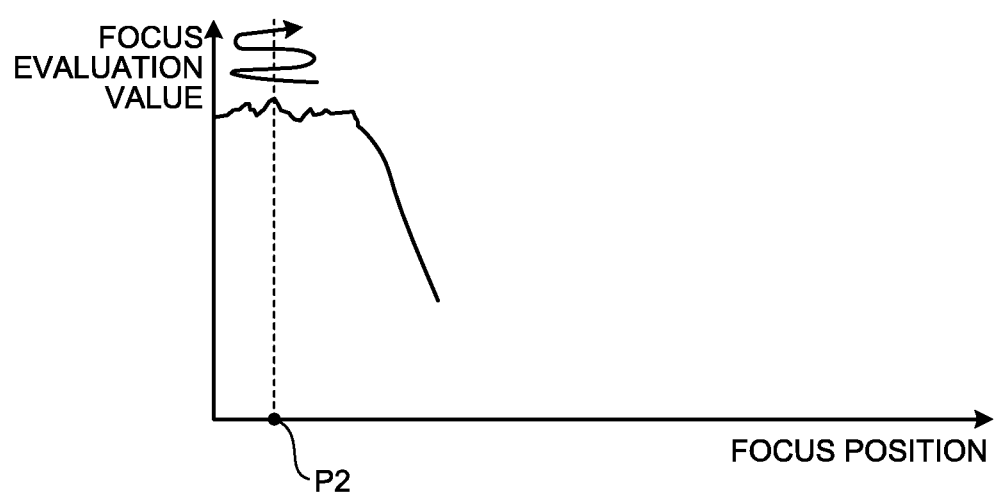
FIG. 7 is a diagram for explaining AF processing performed by the lens control unit.

FIG. 5 to FIG. 7 are diagrams for explaining AF processing performed by the lens control unit 941. Specifically, FIG. 5 is a diagram illustrating a subject distance DS between the distal end of the insertion unit 2 and a subject Su. FIG. 6 is a diagram for explaining AF processing performed by the lens control unit 941 when the subject distance DS is longer than a first reference distance D1. FIG. 7 is a diagram for explaining AF processing performed by the lens control unit 941 when the subject distance DS is within the first reference distance D1.

Specifically, the lens control unit 941 calculates a focus evaluation value for evaluating a focus state of the subject image SI based on the detection information (contrast or frequency components) output from the detection processing unit 922. For example, the lens control unit 941 uses, as the focus evaluation value, contrast detected by the detection processing unit 922 or a sum of high-frequency components among frequency components detected by the detection processing unit 922. The greater the focus evaluation value, the more focused state is indicated.

As illustrated in FIG. 6, the lens control unit 941 sequentially calculates focus evaluation values and sequentially stores, in the storage unit 97, focus information in which a focus position detected by the lens position detection unit 53 and a focus evaluation value corresponding to the focus position are associated, while changing the focus position by operating the lens drive unit 52. Thereafter, the lens control unit 941 calculates a peak position (a focus position P1) at which the focus evaluation value is maximum, based on the plurality of pieces of focus information stored in the storage unit 97. Further, based on the focus position P1 and a current focus position detected by the lens position detection unit 53, the lens control unit 941 calculates a moving direction (a direction toward a near point or a direction toward a far point) and a moving amount for moving the focus lens 511 from the current focus position to the focus position P1. The lens control unit 941 then outputs a control signal corresponding to the moving direction and the moving amount to the lens drive unit 52, and locates the focus lens 511 at the focus position P1. As described above, in the first embodiment, the lens control unit 941 performs the AF processing using a so-called hill climbing method.

Regarding the AF processing described above, it may be possible to adopt so-called continuous AF that is performed continuously or so-called one-touch AF that is performed in accordance with operation on an operation button (not illustrated) provided in the camera head 5 or the like.

When the subject distance DS is within the first reference distance D1 (FIG. 5), the detection area for performing the detection processing is an extremely narrow area of the subject Su. Therefore, accuracy of the detection processing is reduced, and a distinct peak is not present in the focus evaluation values even when the focus position is changed as illustrated in FIG. 7. That is, the lens control unit 941 may calculate a wrong peak position (a focus position P2 (FIG. 7)) at which the subject image SI is not in focus, and locate the focus lens 511 at the focus position P2 in some cases. If one-touch AF is adopted as the AF processing, a doctor or the like repeats operation on the operation button (not illustrated) provided in the camera head 5 or the like in order that the subject image SI becomes in focus. That is, the first reference distance D1 corresponds to the longest subject distance DS among the subject distances DS with which the focus lens 511 is highly likely to be located at the wrong focus position P2 in a case where the subject distances DS are within the first reference distance D1.

The distance determination unit 942 performs first determination processing of comparing the focus position detected by the lens position detection unit 53 with a first threshold, and determining whether the subject distance DS is within the first reference distance D1. Further, the distance determination unit 942 performs second determination processing of comparing the focus position detected by the lens position detection unit 53 with a second threshold, and determining whether the subject distance DS is below a second reference distance D2. In the first embodiment, the distance determination unit 942 performs the first determination processing when the treatment tool detection unit 923 determines that the treatment tool Tt is not included in the subject image SI inside the captured image CI. Further, the distance determination unit 942 performs the second determination processing when the treatment tool detection unit 923 determines that the treatment tool Tt is included in the subject image SI inside the captured image CI.

As illustrated in FIG. 5, the second reference distance D2 corresponds to the shortest subject distance DS among the subject distances DS with which the distal end of the insertion unit 2 does not get dirty by mist Mi that is generated during treatment using the treatment tool Tt, such as an electric scalpel. The first threshold corresponds to a focus position at which the subject image SI becomes in focus when the subject distance DS reaches the first reference distance D1. In the first embodiment, the first threshold is set to "10" (a near point is "0" and a far point is "100"). The second threshold corresponds to a focus position at which the subject image SI becomes in focus when the subject distance DS reaches the second reference distance D2. In the first embodiment, the second threshold is set to "20" (a near point is "0" and a far point is "100"). The first and second thresholds are stored in the storage unit 97 in advance.

That is, the distance determination unit 942 uses a correlation between the focus position and the subject distance DS and compares the focus position with the first threshold or the second threshold to determine whether the subject distance DS is within the first reference distance D1 or the second reference distance D2.

When the distance determination unit 942 determines that the subject distance DS is within the first reference distance D1 or the second reference distance D2, the sound control unit 943 outputs a control signal to the display device 7 (the sound output unit 72) via the second transmission cable 8 and outputs sound from the sound output unit 72.

The display unit 71, the display control unit 93, the sound output unit 72, and the sound control unit 943 described above correspond to a distance information notification unit 100 (FIG. 2).

The input unit 95 is configured using an operating device, such as a mouse, a keyboard, or a touch panel, and accepts operation from a user.

The output unit 96 is configured using a speaker, a printer, or the like, and outputs various kinds of information.

The storage unit 97 stores therein a program to be executed by the control unit 94, information needed for processing performed by the control unit 94, and the like.

Operation of Endoscope Device

Next, operation of the endoscope device 1 described above will be explained.

Figure 8:
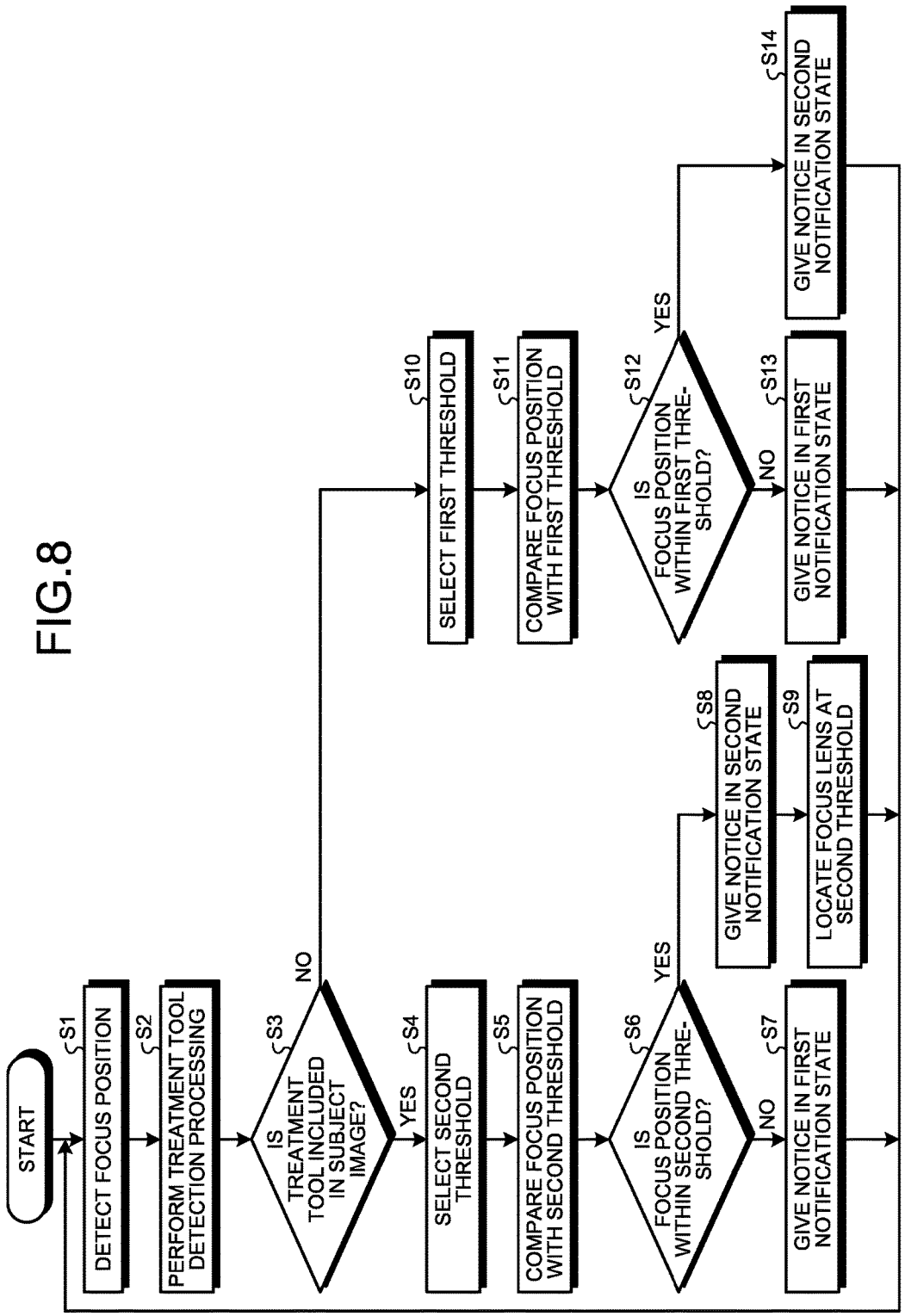
FIG. 8 is a flowchart illustrating operation of the endoscope device.

FIG. 8 is a flowchart illustrating operation of the endoscope device 1.

Hereinafter, operation of the lens position detection unit 53, the treatment tool detection unit 923, the distance determination unit 942, and the distance information notification unit 100 will be mainly described.

First, the lens position detection unit 53 detects a focus position under the control of the control device 9 (Step S1).

After Step S1, the treatment tool detection unit 923 performs the treatment tool detection processing (Step S2), and determines whether the treatment tool Tt is included in the subject image SI inside the captured image CI (Step S3).

If it is determined that the treatment tool Tt is included (Yes at Step S3), the distance determination unit 942 selects the second threshold from among the first and second thresholds stored in the storage unit 97 (Step S4), and performs the second determination processing (Steps S5 and S6).

Specifically, the distance determination unit 942 compares the focus position detected at Step S1 with the second threshold (Step S5), and determines whether the focus position is within the second threshold (whether the subject distance DS is within the second reference distance D2) (Step S6).

If it is determined that the focus position exceeds the second threshold (No at Step S6), the distance information notification unit 100 gives a notice of distance information on the subject distance DS in a first notification state (Step S7). Thereafter, the endoscope device 1 returns to Step S1.

Figure 9:
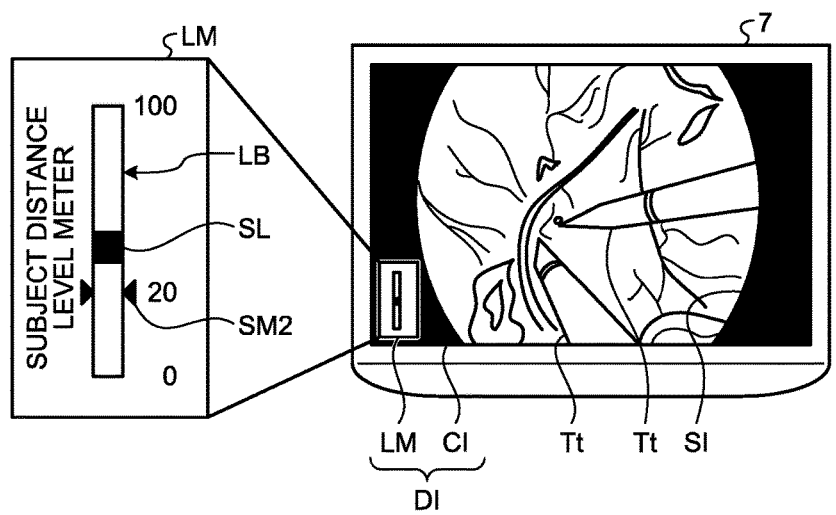
FIG. 9 is a diagram illustrating an example of a first notification state at Step S7.

FIG. 9 is a diagram illustrating an example of the first notification state at Step S7.

For example, at Step S7, the distance information notification unit 100 gives a notice of the distance information on the subject distance DS in the first notification state as illustrated in FIG. 9.

Specifically, as illustrated in FIG. 9, the display control unit 93 displays a display image DI, in which a subject distance level meter LM is superimposed on the captured image CI, on the display device 7 (the display unit 71).

As illustrated in FIG. 9, a level bar LB, a slider SL, and a second threshold mark SM2 are arranged in the subject distance level meter LM.

The level bar LB is a scale corresponding to the range of the focus position ("0" to "100") in which the focus lens 511 is movable.

The slider SL indicates a position on the level bar LB corresponding to the focus position detected at Step S1. In the example in FIG. 9, the slider SL is located at a certain position on the level bar LB corresponding to the focus position because the focus position detected at Step S1 exceeds the second threshold ("20") (No at Step S6).

The second threshold mark SM2 is a mark indicating the second threshold ("20").

In contrast, at Step S6, if it is determined that the focus position is within the second threshold (Yes at Step S6), the distance information notification unit 100 gives a notice of the distance information on the subject distance DS in a second notification state that is different from the first notification state used at Step S7 (Step S8).

Figure 10:
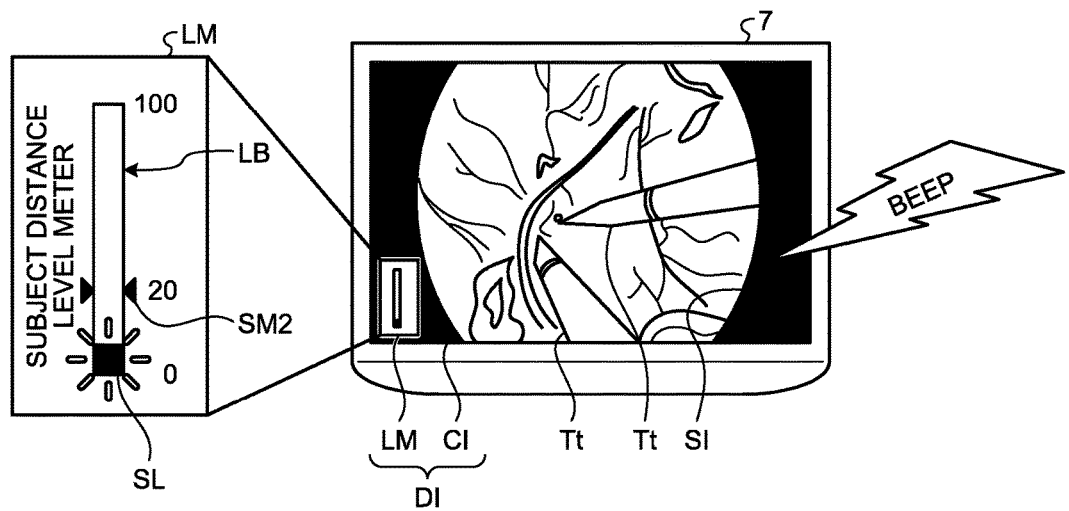
FIG. 10 is a diagram illustrating an example of a second notification state at Step S8.

FIG. 10 is a diagram illustrating an example of the second notification state at Step S8.

For example, at Step S8, the distance information notification unit 100 gives a notice of the distance information on the subject distance DS in the second notification state as illustrated in FIG. 10.

Specifically, as illustrated in FIG. 10, the display control unit 93 displays the display image DI, in which the subject distance level meter LM is superimposed on the captured image CI, on the display device 7 (the display unit 71), similarly to the first notification state described above (FIG. 9).

In the subject distance level meter LM in the second notification state, as illustrated in FIG. 10, the slider SL indicates a position on the level bar LB corresponding to the focus position detected at Step S1, and is displayed in a blinking manner. In the example in FIG. 10, the slider SL is located at a certain position on the level bar LB corresponding to the focus position because the focus position detected at Step S1 is within the second threshold ("20") (Yes at Step S6).

Further, as illustrated in FIG. 10, the sound control unit 943 generates an alarm sound (beep sound in the example in FIG. 10) from the display device 7 (the sound output unit 72).

The subject distance level meter LM illustrated in FIG. 9 corresponds to the distance information in the first notification state. The subject distance level meter LM and the alarm sound illustrated in FIG. 10 correspond to the distance information in the second notification state. That is, the distance information notification unit 100 gives a notice of the distance information in different notification states (the first and second notification states) between when the distance determination unit 942 determines that the subject distance DS exceeds the second reference distance D2 and when the distance determination unit 942 determines that the subject distance DS is within the second reference distance D2.

After Step S8, the lens control unit 941 calculates a moving direction (direction toward a far point) and a moving amount for moving the focus lens 511 from the focus position detected at Step S1 to the second threshold, based on the focus position detected at Step S1 and the second threshold. The lens control unit 941 outputs a controls signal corresponding to the moving direction and the moving amount to the lens drive unit 52, and locates the focus lens 511 at the second threshold (Step S9). Thereafter, the endoscope device 1 returns to Step S1.

At Step S3, if it is determined that the treatment tool Tt is not included (No at Step S3), the distance determination unit 942 selects the first threshold from among the first and second thresholds stored in the storage unit 97 (Step S10), and performs the first determination processing (Steps S11 and S12).

Specifically, the distance determination unit 942 compares the focus position detected at Step S1 with the first threshold (Step S11), and determines whether the focus position is within the first threshold (whether the subject distance DS is within the first reference distance D1) (Step S12).

If it is determined that the focus position exceeds the first threshold (No at Step S12), the distance information notification unit 100 gives a notice of the distance information on the subject distance DS in a first notification state (Step S13). Thereafter, the endoscope device 1 returns to Step S1.

Figure 11:
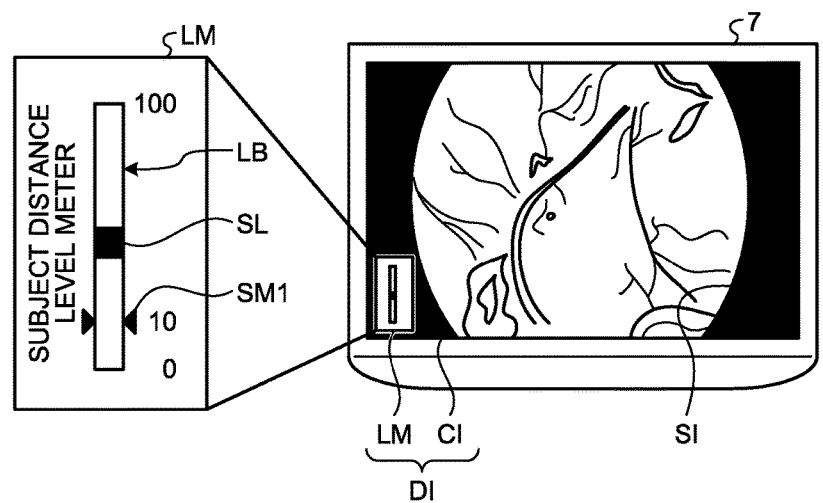
FIG. 11 is a diagram illustrating an example of a first notification state at Step S13.

FIG. 11 is a diagram illustrating an example of the first notification state at Step S13.

For example, at Step S13, the distance information notification unit 100 gives a notice of the distance information on the subject distance DS in the first notification state as illustrated in FIG. 11, similarly to the case in FIG. 9 described above.

As illustrated in FIG. 11, the second threshold mark SM2 is omitted and a first threshold mark SM1 indicating the first threshold ("10") is added in the subject distance level meter LM at Step S13, as compared to the subject distance level meter LM illustrated in FIG. 9.

In contrast, if it is determined that the focus position is within the first threshold (Yes at Step S12), the distance information notification unit 100 gives a notice of the distance information on the subject distance DS in a second notification state that is different from the first notification state used at Step S13 (Step S14). Thereafter, the endoscope device 1 returns to Step S1.

Figure 12:
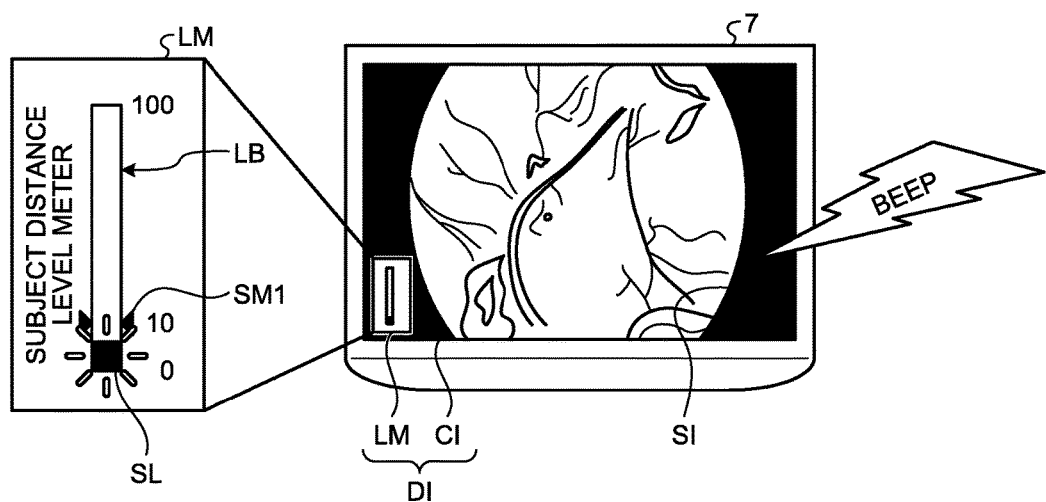
FIG. 12 is a diagram illustrating an example of a second notification state at Step S14.

FIG. 12 is a diagram illustrating an example of the second notification state at Step S14.

For example, at Step S14, the distance information notification unit 100 gives a notice of the distance information on the subject distance DS in the second notification state as illustrated in FIG. 12, similarly to the case illustrated in FIG. 10 described above.

As illustrated in FIG. 12, the first threshold mark SM1 is arranged instead of the second threshold mark SM2 in the subject distance level meter LM displayed at Step S14, similarly to the subject distance level meter LM illustrated in FIG. 11.

The subject distance level meter LM illustrated in FIG. 11 corresponds to the distance information in the first notification state. The subject distance level meter LM and the alarm sound illustrated in FIG. 12 correspond to the distance information in the second notification state. That is, the distance information notification unit 100 gives a notice of the distance information in different notification states (the first and second notification states) between when the distance determination unit 942 determines that the subject distance DS exceeds the first reference distance D1 and when the distance determination unit 942 determines that the subject distance DS is within the first reference distance D1.

According to the first embodiment described above, the following effects are achieved.

The endoscope device 1 according to the first embodiment determines whether the subject distance DS is within the second reference distance D2 based on the focus position, by use of a correlation between the focus position and the subject distance DS. That is, the endoscope device 1 determines, based on the focus position, whether the distal end of the insertion unit 2 is positioned within a range in which the distal end gets dirty by the mist Mi that is generated during treatment using the treatment tool Tt. The endoscope device 1 gives a notice of the distance information on the subject distance DS in different notification states (the first notification state (FIG. 9) and the second notification state (FIG. 10)) between when the subject distance DS exceeds the second reference distance D2 and when the subject distance DS is within the second reference distance D2.

Therefore, by recognizing a change of the notification state of the distance information, a doctor or the like can determine whether the distal end of the insertion unit 2 is positioned within a range in which the distal end gets dirty by the mist Mi that is generated during treatment using the treatment tool Tt. When determining that the distal end of the insertion unit 2 is positioned within this range and when performing treatment using the treatment tool Tt, the doctor or the like can prevent the distal end of the insertion unit 2 from getting dirty by the mist Mi by keeping the distal end of the insertion unit 2 away from the subject Su. Therefore, it is possible to prevent the doctor or the like from performing cumbersome operation of pulling the insertion unit 2 out of a living body and removing dirt from the distal end of the insertion unit 2.

Further, the endoscope device 1 according to the first embodiment determines whether the subject distance DS is within the first reference distance D1 based on the focus position, by use of a correlation between the focus position and the subject distance DS. That is, the endoscope device 1 determines, based on the focus position, whether the distal end of the insertion unit 2 is positioned within a range in which the focus lens 511 is highly likely to be located at the wrong focus position P2 (position at which the subject image SI is not in focus). The endoscope device 1 gives a notice of the distance information on the subject distance DS in different notification states (the first notification state (FIG. 11) and the second notification state (FIG. 12)) between when the subject distance DS exceeds the first reference distance D1 and when the subject distance DS is within the first reference distance D1.

Therefore, by recognizing a change of the notification state of the distance information, a doctor or the like can determine whether the distal end of the insertion unit 2 is positioned within a range in which the focus lens 511 is highly likely to be located at the wrong focus position P2. When determining that the distal end of the insertion unit 2 is positioned within this range, the doctor or the like can keep the distal end of the insertion unit 2 away from the subject Su. Consequently, in a case where one-touch AF is adopted as AF processing, the doctor or the like can be prevented from performing a cumbersome operation of repeatedly operating an operation button (not illustrated) provided in the camera head 5 or the like in order that the subject image SI becomes in focus.

As described above, according to the endoscope device 1 of the first embodiment, it is possible to improve usability.

Further, the endoscope device 1 according to the first embodiment performs the first determination processing using the first threshold when the treatment tool Tt is not used, and performs the second determination processing using the second threshold when the treatment tool Tt is used.

Therefore, it is possible to urge a doctor or the like to keep the distal end of the insertion unit 2 away from the subject Su such that the subject distance DS becomes longer than the second reference distance D2 only when the treatment tool Tt is used and the distal end of the insertion unit 2 is likely to get dirty by the mist Mi. That is, when the treatment tool Tt is not used and the distal end of the insertion unit 2 can hardly get dirty by the mist Mi, the doctor or the like is not urged as described above, but can set the subject distance DS to the preferred subject distance DS that may be shorter than the second reference distance D2.

In particular, in the treatment tool detection processing, the non-used state and the used state of the treatment tool Tt are detected by image processing (pattern matching). That is, the non-used state and the used state of the treatment tool Tt are automatically detected by the endoscope device 1. Therefore, as compared to a configuration in which an operation button is provided in the endoscope device 1 and the endoscope device 1 detects the used state of the treatment tool Tt in accordance with operation on the operation button performed by a doctor or the like for example, it is not necessary to urge the doctor or the like to perform this operation, and therefore, it is possible to improve usability.

Further, when the subject distance DS is within the second reference distance D2, the endoscope device 1 according to the first embodiment locates the focus lens 511 at the second threshold at which the subject image SI becomes in focus at the second reference distance D2.

Therefore, a doctor or the like can easily locate the distal end of the insertion unit 2 at a position at which the distal end is less likely to get dirty by the mist Mi, by moving the distal end of the insertion unit 2 away from the subject Su until the subject image SI becomes in focus while checking the display image DI displayed on the display device 7 (the display unit 71).

Moreover, the endoscope device 1 according to the first embodiment includes the zoom lens 512 that changes the angle of view. That is, when the subject image SI is enlarged by the zoom lens 512, it is difficult for a doctor or the like to determine whether the distal end of the insertion unit 2 is positioned excessively close to the subject Su only by checking the display image DI. Therefore, by applying the technology disclosed herein to the endoscope device 1 including the zoom lens 512, it becomes possible to achieve the effect to improve usability in a preferred manner.

Second Embodiment

Next, a second embodiment will be described.

In the following description, the same components as those of the first embodiment described above are denoted by the same reference signs, and detailed explanation thereof will be omitted or simplified.

Figure 13:
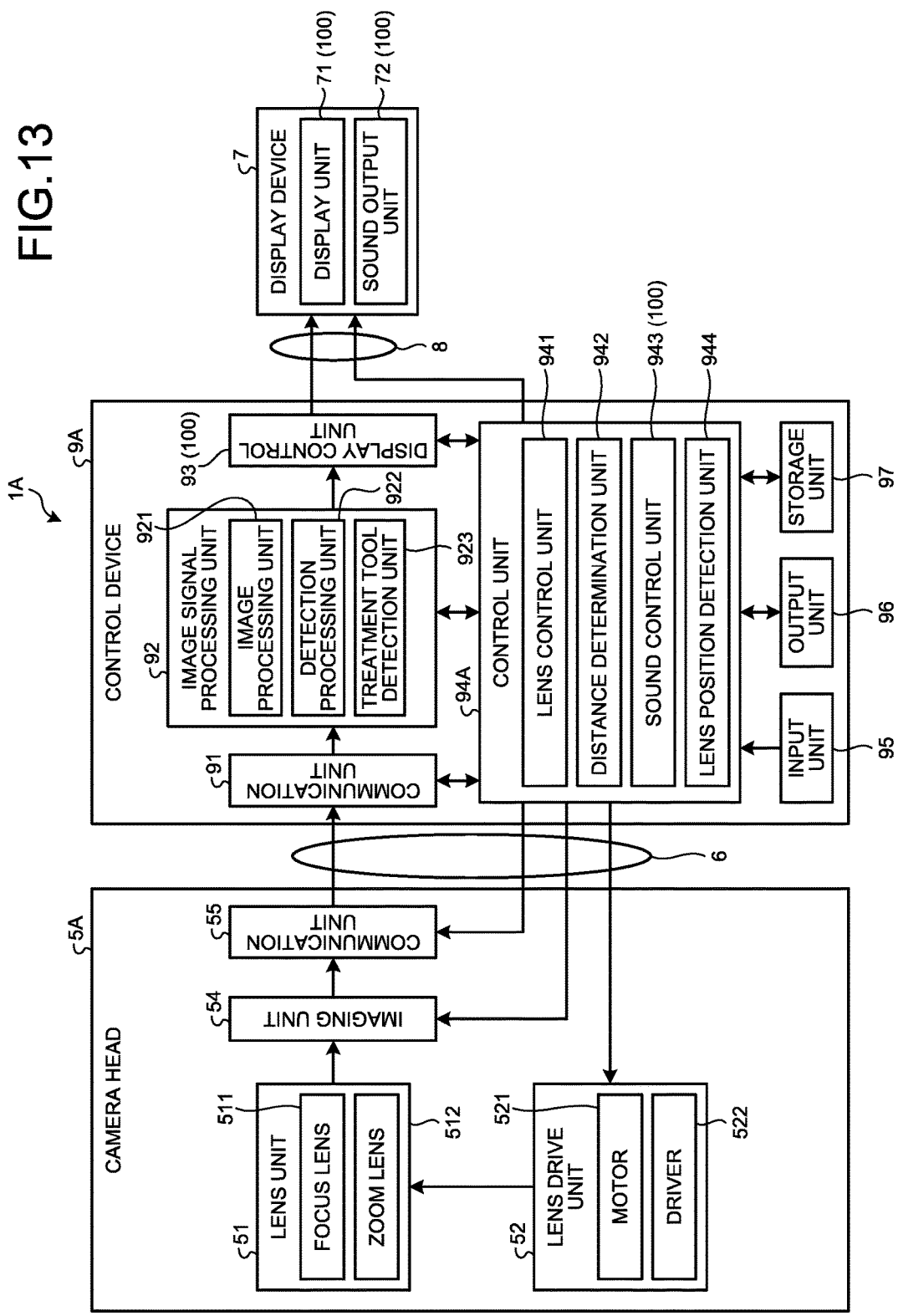
FIG. 13 is a diagram illustrating a schematic configuration of an endoscope device according to a second embodiment.

FIG. 13 is a diagram corresponding to FIG. 2, and illustrates a schematic configuration of an endoscope device 1A according to the second embodiment.

As illustrated in FIG. 13, the endoscope device 1A according to the second embodiment includes a camera head 5A that is configured by removing the lens position detection unit 53 from the camera head 5 of the endoscope device 1 of the first embodiment described above, and a control device 9A (a control unit 94A) that is configured by adding a lens position detection unit 944 to the control device 9 (the control unit 94).

The motor 521 according to the second embodiment is configured with a stepping motor.

The storage unit 97 according to the second embodiment stores therein, in advance, an initial rotation position of the motor 521, and sequentially stores therein (updates), as the latest rotation amount, a rotation amount of the motor 521 when the motor 521 rotates under the control of the lens control unit 941.

When moving the focus lens 511 to a desired focus position, the lens control unit 941 according to the second embodiment calculates a focus position located before movement, from the initial rotation position and the rotation amount stored in the storage unit 97. Thereafter, the lens control unit 941 calculates a rotation direction and a rotation amount of the motor 521 for moving the focus lens 511 from the focus position located before movement to the desired focus position, based on the desired focus position and the focus position located before movement. The lens control unit 941 then outputs a control signal corresponding to the rotation direction and the rotation amount to the lens drive unit 52, and locates the focus lens 511 at the desired focus position. The lens control unit 941 updates the rotation amount stored in the storage unit 97 with the latest rotation amount.

The lens position detection unit 944 detects (calculates) a lens position at which the focus lens 511 is located, based on the initial rotation amount and the rotation amount stored in the storage unit 97 and based on the control signal (control values (the rotation direction and the rotation amount of the motor 521)) output from the lens control unit 941 to the lens drive unit 52.

The processing performed by the lens position detection unit 944 as described above is performed at Step S1 described in the first embodiment.

According to the second embodiment described above, it is possible to achieve the same effects as those of the first embodiment described above.

Third Embodiment

Next, a third embodiment will be described.

In the following description, the same components as those of the first embodiment described above are denoted by the same reference signs, and detailed explanation thereof will be omitted or simplified.

Figure 14:
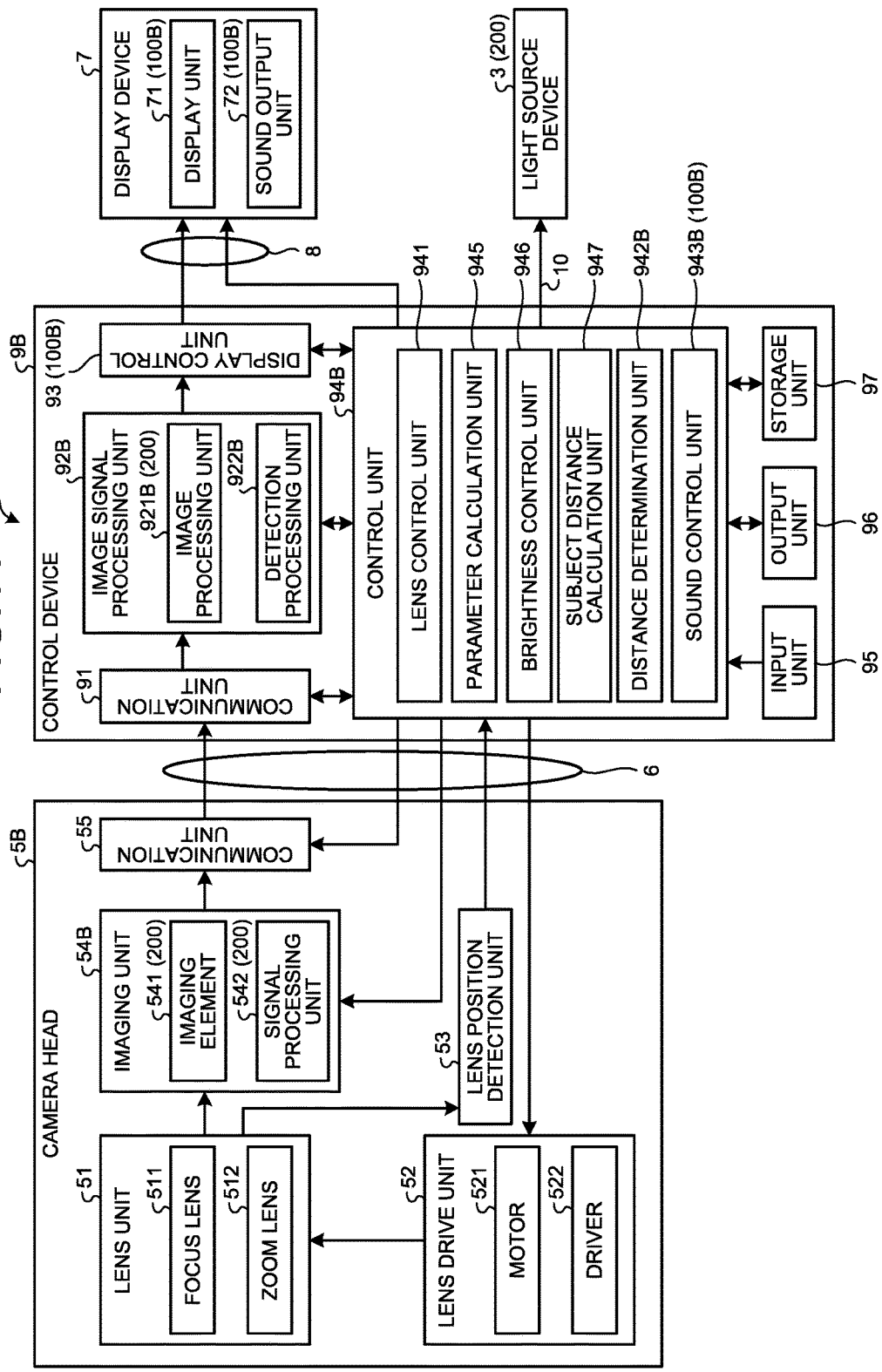
FIG. 14 is a diagram illustrating a schematic configuration of an endoscope device according to a third embodiment.

FIG. 14 is a diagram corresponding to FIG. 2, and illustrates a schematic configuration of an endoscope device 1B according to the third embodiment.

As illustrated in FIG. 14, the endoscope device 1B according to the third embodiment includes a camera head 5B and a control device 9B, which have different functions from those of the camera head 5 and the control device 9 of the endoscope device 1 of the first embodiment described above.

As illustrated in FIG. 14, the camera head 5B according to the third embodiment includes an imaging unit 54B instead of the imaging unit 54 of the camera head 5 of the first embodiment described above.

The imaging unit 54B captures an image inside a living body under the control of the control device 9B. As illustrated in FIG. 14, the imaging unit 54B includes an imaging element 541 and a signal processing unit 542.

The imaging element 541 is configured with a CCD, a CMOS, or the like, which receives the subject image SI condensed by the insertion unit 2 and formed by the lens unit 51 and converts the subject image to an electrical signal (analog signal).

The signal processing unit 542 performs signal processing on the electrical signal (analog signal) output from the imaging element 541, and outputs an image signal (RAW signal (digital signal)).

For example, the signal processing unit 542 performs signal processing, such as reset noise reduction processing, analog gain multiplication processing for amplifying the analog signal, or A/D conversion, on the electrical signal (analog signal) output from the imaging element 541.

As illustrated in FIG. 14, the control device 9B according to the third embodiment includes an image signal processing unit 92B and a control unit 94B, which have different functions from those of the image signal processing unit 92 and the control unit 94 of the control device 9 of the first embodiment described above.

As illustrated in FIG. 14, the image signal processing unit 92B is configured by removing the treatment tool detection unit 923 from the image signal processing unit 92 of the first embodiment described above, and including an image processing unit 921B and a detection processing unit 922B that have different functions as those of the image processing unit 921 and the detection processing unit 922.

The image processing unit 921B multiplies an image signal (RAW signal (digital signal)) received by the communication unit 91 by digital gain for amplifying the digital signal. That is, the image processing unit 921B has a function as a digital gain multiplication unit. The image processing unit 921B performs RAW processing, RGB processing, and YC processing on the image signal (RAW signal (digital signal)) multiplied by the digital gain, similarly to the image processing unit 921 of the first embodiment described above.

Based on pixel information (luminance signal (Y signal)) on each of pixels in a detection area in the whole captured image CI of one frame captured by the imaging element 541, the detection processing unit 922B detects detects contrast or frequency components of an image in the detection area similarly to the detection processing unit 922 of the first embodiment described above, and further detects a luminance average value of the image in the detection area. The detection processing unit 922B outputs detection information (the contrast or frequency components, and the luminance average value) obtained by the detection to the control unit 94B.

As illustrated in FIG. 14, the control unit 94B includes a distance determination unit 942B and a sound control unit 943B, which have different functions as those of the distance determination unit 942 and the sound control unit 943 of the control unit 94 of the first embodiment described above, and further includes functions of a parameter calculation unit 945, a brightness control unit 946, and a subject distance calculation unit 947.

The parameter calculation unit 945 calculates a brightness parameter for changing brightness of the captured image CI, which is obtained by imaging performed by the imaging unit 54B, to reference brightness (changing the luminance average value obtained by the detection processing to a reference luminance average value) based on the detection information (luminance average value) output from the detection processing unit 922B.

In the third embodiment, the parameter calculation unit 945 calculates four brightness parameters such as an exposure time of each of pixels in the imaging element 541, analog gain for multiplication performed by the signal processing unit 542, digital gain for multiplication performed by the image processing unit 921B, and an amount of light supplied from the light source device 3 to the insertion unit 2.

Figure 15:
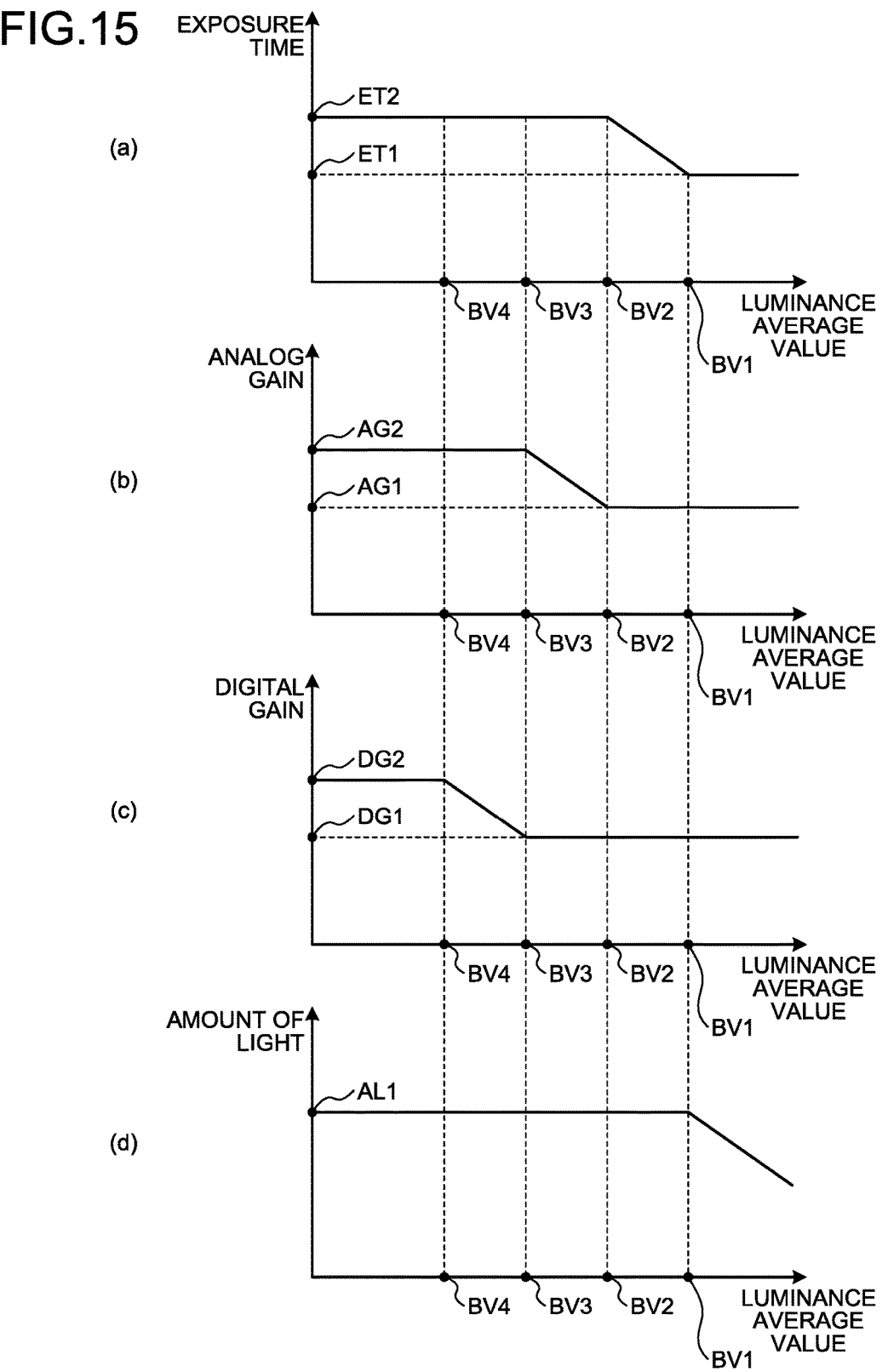
FIG. 15 is a diagram illustrating examples of relationships between brightness parameters and a luminance average value.

FIG. 15 is a diagram illustrating examples of relationships between the brightness parameters and the luminance average value. Specifically, a part (a) of FIG. 15 illustrates a relationship between the exposure time and the luminance average value. A part (b) of FIG. 15 illustrates a relationship between the analog gain and the luminance average value. A part (c) of FIG. 15 illustrates a relationship between the digital gain and the luminance average value. A part (d) of FIG. 15 illustrates a relationship between the amount of light and the luminance average value. The horizontal axis in FIG. 15 indicates the luminance average value, where the luminance average value increases to the right (the luminance average value decreases to the left).

Specifically, the parameter calculation unit 945 calculates an exposure time (brightness parameter) corresponding to the detection information (luminance average value) output from the detection processing unit 922B, by use of the relationship illustrated in the part (a) of FIG. 15 for example. In the part (a) of FIG. 15, a luminance average value BV1 is a value higher than a luminance average value BV2. In addition, an exposure time ET1 is a time shorter than an exposure time ET2. In the example in the part (a) of FIG. 15, as the relationship between the exposure time and the luminance average value, a relationship is illustrated in which the exposure time ET1 is used for luminance average values higher than the luminance average value BV1, the exposure time ET2 is used for luminance average values lower than the luminance average value BV2, and the exposure time is increased from the exposure time ET1 to the exposure time ET2 at a constant rate for luminance average values from the luminance average value BV1 to the luminance average value BV2.

The parameter calculation unit 945 further calculates analog gain (brightness parameter) corresponding to the detection information (luminance average value) output from the detection processing unit 922B, by use of the relationship illustrated in the part (b) of FIG. 15 for example. In the part (b) of FIG. 15, a luminance average value BV3 is a value lower than the luminance average value BV2. In addition, analog gain AG1 is a value smaller than analog gain AG2. In the example in the part (b) of FIG. 15, as the relationship between the analog gain and the luminance average value, a relationship is illustrated in which the analog gain AG1 is used for luminance average values higher than the luminance average value BV2, the analog gain AG2 is used for luminance average values lower than the luminance average value BV3, and the analog gain is increased from the analog gain AG1 to the analog gain AG2 at a constant rate for luminance average values from the luminance average value BV2 to the luminance average value BV3.

The parameter calculation unit 945 further calculates digital gain (brightness parameter) corresponding to the detection information (luminance average value) output from the detection processing unit 922B, by use of the relationship illustrated in the part (c) of FIG. 15 for example. In the part (c) of FIG. 15, a luminance average value BV4 is a value lower than the luminance average value BV3. In addition, digital gain DG1 is a value smaller than digital gain DG2. In the example in the part (c) of FIG. 15, as the relationship between the digital gain and the luminance average value, a relationship is illustrated in which the digital gain DG1 is used for luminance average values higher than the luminance average value BV3, the digital gain DG2 is used for luminance average values lower than the luminance average value BV4, and the digital gain is increased from the digital gain DG1 to the digital gain DG2 at a constant rate for luminance average values from the luminance average value BV3 to the luminance average value BV4.

The parameter calculation unit 945 further calculates an amount of light (brightness parameter) corresponding to the detection information (luminance average value) output from the detection processing unit 922B, by use of the relationship illustrated in The part (d) of FIG. 15 for example. In the example in The part (d) of FIG. 15, as the relationship between the amount of light and the luminance average value, a relationship is illustrated in which an amount of light AL1 is used for luminance average values lower than the luminance average value BV1, and the amount of light is decreased from the amount of light AL1 at a constant rate as a luminance average value increases from the luminance average value BV1.

The relationships between the brightness parameters and the luminance average value (for example, the relationships illustrated in FIG. 15) are stored in the storage unit 97 in advance as a look-up table (LUT) or the like, for example.

The brightness control unit 946 controls operation of the imaging element 541, the signal processing unit 542, the image processing unit 921B, and the light source device 3 based on the brightness parameters calculated by the parameter calculation unit 945.

Specifically, the brightness control unit 946 outputs a control signal to the imaging unit 54B via the first transmission cable 6, and sets the exposure time of each of the pixels of the imaging element 541 to the exposure time (brightness parameter) calculated by the parameter calculation unit 945. The brightness control unit 946 further outputs a control signal to the imaging unit 54B via the first transmission cable 6, and sets the analog gain used for multiplication performed by the signal processing unit 542 to the analog gain (brightness parameter) calculated by the parameter calculation unit 945. The brightness control unit 946 further outputs a control signal to the image processing unit 921B, and sets the digital gain used for multiplication performed by the image processing unit 921B to the digital gain (brightness parameter) calculated by the parameter calculation unit 945. The brightness control unit 946 further outputs a control signal to the light source device 3 via the third transmission cable 10, and sets the amount of light supplied from the light source device 3 to the insertion unit 2 to the amount of light (brightness parameter) calculated by the parameter calculation unit 945.

That is, the imaging element 541, the signal processing unit 542, the image processing unit 921B, and the light source device 3 correspond to a brightness change unit 200 (FIG. 14) that changes brightness of the captured image CI obtained by imaging performed by the imaging unit 54B.

The subject distance calculation unit 947 calculates the subject distance DS.

If the subject distance DS is changed without changing the brightness of the captured image CI to the reference brightness (in a state where the brightness parameters are maintained at reference brightness parameters) by the brightness change unit 200, the detection processing unit 922B detects a higher luminance average value as the subject distance DS decreases. That is, the subject distance DS and the luminance average value have a correlation with each other. Therefore, with use of this correlation, it is possible to calculate the subject distance DS from the luminance average value. However, as described above, the brightness of the captured image CI is changed to the reference brightness by the brightness change unit 200. That is, even when the subject distance DS is changed, the luminance average value detected by the detection processing unit 922B is maintained constant at the reference luminance average value. Therefore, even if the correlation described above is used, it is difficult to calculate the subject distance DS from the luminance average value.

The brightness parameters calculated by the parameter calculation unit 945 are calculated based on the luminance average value that is detected by the detection processing unit 922B before the brightness change unit 200 changes the brightness of the captured image CI to the reference brightness. Therefore, it is possible to calculate, from the brightness parameters, a luminance average value that was present before the brightness of the captured image CI was changed to the reference brightness, and it is eventually possible to calculate the subject distance DS.

Therefore, the subject distance calculation unit 947 converts the brightness parameters calculated by the parameter calculation unit 945 to the subject distance DS using a predetermined relational expression or LUT.

In the third embodiment, the subject distance calculation unit 947 calculates the subject distance DS in a range from "0" to "100", where "0" indicates a state in which the distal end of the insertion unit 2 is in contact with the subject Su and "100" indicates a state in which the distal end of the insertion unit 2 is adequately separated from the subject Su.

The distance determination unit 942B compares the subject distance DS calculated by the subject distance calculation unit 947 with a reference distance, and determines whether the subject distance DS is within the reference distance.

The reference distance corresponds to the longest subject distance DS among the subject distances DS with which the focus lens 511 is highly likely to be located at the wrong focus position P2 in a case where the subject distances DS are within the reference distance. Further, the reference distance corresponds to the shortest subject distance DS among the subject distances DS with which the distal end of the insertion unit 2 does not get dirty by the mist Mi that is generated during treatment using the treatment tool Tt, such as an electric scalpel.

In the third embodiment, the reference distance is set to "20" (the range of the subject distance DS is from "0" to "100"). The reference distance is stored in the storage unit 97 in advance.

When the distance determination unit 942B determines that the subject distance DS is within the reference distance, the sound control unit 943B outputs a control signal to the display device 7 (the sound output unit 72) via the second transmission cable 8 and outputs sound from the sound output unit 72.

The display unit 71, the display control unit 93, the sound output unit 72, and the sound control unit 943B described above correspond to a distance information notification unit 100B (FIG. 14).

Next, operation of the endoscope device 1B described above will be explained.

Figure 16:
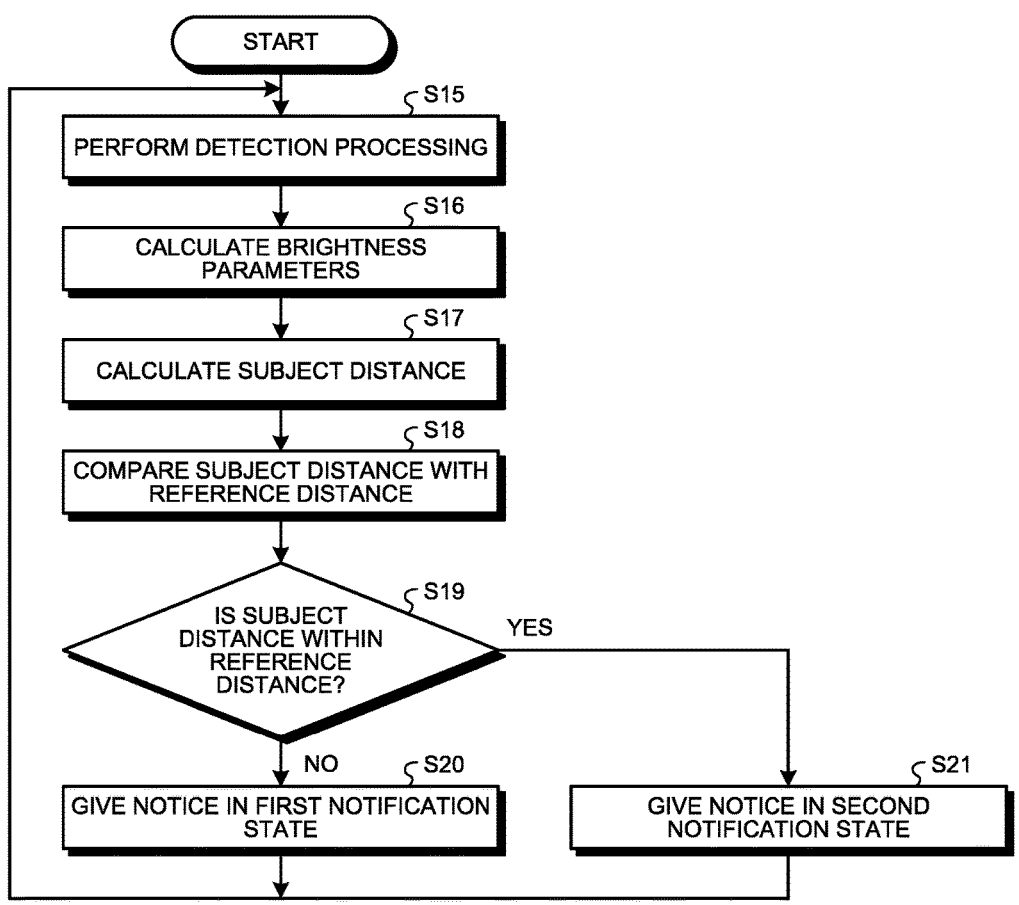
FIG. 16 is a flowchart illustrating operation of the endoscope device.

FIG. 16 is a flowchart illustrating operation of the endoscope device 1B.

Hereinafter, operation of the detection processing unit 922B, the parameter calculation unit 945, the subject distance calculation unit 947, the distance determination unit 942B, and the distance information notification unit 100B will be mainly described.

First, the detection processing unit 922B performs the detection processing under the control of the control unit 94B (Step S15). The detection processing unit 922B outputs detection information obtained by the detection processing to the control unit 94B.

After Step S15, the parameter calculation unit 945 calculates the brightness parameters (the exposure time, the analog gain, the digital gain, and the amount of light) based on the detection information (luminance average value) that is obtained by the detection processing at Step S15 (Step S16).

After Step S16, the subject distance calculation unit 947 calculates the subject distance DS (in the range from "0" to "100") based on the brightness parameters (the exposure time, the analog gain, the digital gain, and the amount of light) calculated at Step S16 (Step S17).

After Step S17, the distance determination unit 942B compares the subject distance DS calculated at Step S17 with the reference distance (Step S18), and determines whether the subject distance DS is within the reference distance (Step S19).

If it is determined that the subject distance DS exceeds the reference distance (No at Step S19), the distance information notification unit 100B gives a notice of distance information on the subject distance DS in the first notification state (Step S20). Thereafter, the endoscope device 1B returns to Step S15.

For example, at Step S20, the distance information notification unit 100B gives a notice of the distance information on the subject distance DS in the first notification state as illustrated in FIG. 9. In the third embodiment, the level bar LB illustrated in FIG. 9 is a scale corresponding to the range of the subject distance DS ("0" to "100"). Further, the slider SL illustrated in FIG. 9 indicates a position on the level bar LB corresponding to the subject distance DS calculated at Step S17. Furthermore, the second threshold mark SM2 illustrated in FIG. 9 indicates the reference distance ("20") of the third embodiment.

In contrast, at Step S19, if it is determined that the subject distance DS is within the reference distance (Yes at Step S19), the distance information notification unit 100B gives a notice of the distance information on the subject distance DS in the second notification state that is different from the first notification state used at Step S20 (Step S21). Thereafter, the endoscope device 1B returns to Step S15.

For example, at Step S21, the distance information notification unit 100B gives a notice of the distance information on the subject distance DS in the second notification state as illustrated in FIG. 10. In the third embodiment, the level bar LB illustrated in FIG. 10 is a scale corresponding to the range of the subject distance DS ("0" to "100"). Further, the slider SL illustrated in FIG. 10 indicates a position on the level bar LB corresponding to the subject distance DS calculated at Step S17. Furthermore, the second threshold mark SM2 illustrated in FIG. 10 indicates the reference distance ("20") of the third embodiment. Moreover, as illustrated in FIG. 10, the distance information notification unit 100B (the sound control unit 943B) outputs an alarm sound (beep sound in the example in FIG. 10) from the display device 7 (the sound output unit 72).

That is, the distance information notification unit 100B gives a notice of the distance information (the subject distance level meter LM and the alarm sound illustrated in FIG. 9 and FIG. 10) in different notification states (the first and second notification states) between when the distance determination unit 942B determines that the subject distance DS exceeds the reference distance and when the distance determination unit 942B determines that the subject distance DS is within the reference distance.

According to the third embodiment described above, the following effects are achieved.

The endoscope device 1B according to the third embodiment converts the brightness parameters to the subject distance DS using a predetermined relational expression or LUT. The endoscope device 1B further determines whether the subject distance DS is within the reference distance. That is, the endoscope device 1B determines whether the distal end of the insertion unit 2 is positioned within a range in which the distal end gets dirty by the mist Mi that is generated during treatment using the treatment tool Tt or within a range in which the focus lens 511 is located at the wrong focus position P2 (position at which the subject image SI is out of focus). The endoscope device 1B gives a notice of the distance information on the subject distance DS in different notification states (the first notification state (FIG. 9) and the second notification state (FIG. 10)) between when the subject distance DS exceeds the reference distance and when the subject distance DS is within the reference distance.

Therefore, by recognizing a change of the notification state of the distance information, a doctor or the like can determine whether the distal end of the insertion unit 2 is positioned within a range in which the distal end gets dirty by the mist Mi that is generated during treatment using the treatment tool Tt. When determining that the distal end of the insertion unit 2 is positioned within this range and when performing treatment using the treatment tool Tt, the doctor or the like can prevent the distal end of the insertion unit 2 from getting dirty by the mist Mi by keeping the distal end of the insertion unit 2 away from the subject Su. Therefore, it is possible to prevent the doctor or the like from performing a cumbersome operation of pulling the insertion unit 2 out of the living body and removing dirt from the distal end of the insertion unit 2.

Further, by recognizing a change of the notification state of the distance information, a doctor or the like can determine whether the distal end of the insertion unit 2 is positioned within a range in which the focus lens 511 is highly likely to be located at the wrong focus position P2. When determining that the distal end of the insertion unit 2 is positioned within this range, the doctor or the like can keep the distal end of the insertion unit 2 away from the subject Su. Consequently, in a case where one-touch AF is adopted as AF processing, the doctor or the like can be prevented from performing a cumbersome operation of repeatedly operating an operation button (not illustrated) provided in the camera head 5 or the like in order that the subject image SI becomes in focus.

As described above, according to the endoscope device 1B of the third embodiment, it is possible to improve usability.

Further, the endoscope device 1B according to the third embodiment includes the zoom lens 512 that changes the angle of view. That is, when the subject image SI is enlarged by the zoom lens 512, it is difficult for a doctor or the like to determine whether the distal end of the insertion unit 2 is positioned excessively close to the subject Su only by checking the display image DI. Therefore, by applying the technology disclosed herein to the endoscope device 1 including the zoom lens 512, it becomes possible to achieve the effect to improve usability in a preferred manner.

Fourth Embodiment

Next, a fourth embodiment will be described.

In the following description, the same components as those of the third embodiment described above are denoted by the same reference signs, and detailed explanation thereof will be omitted or simplified.

Figure 17:
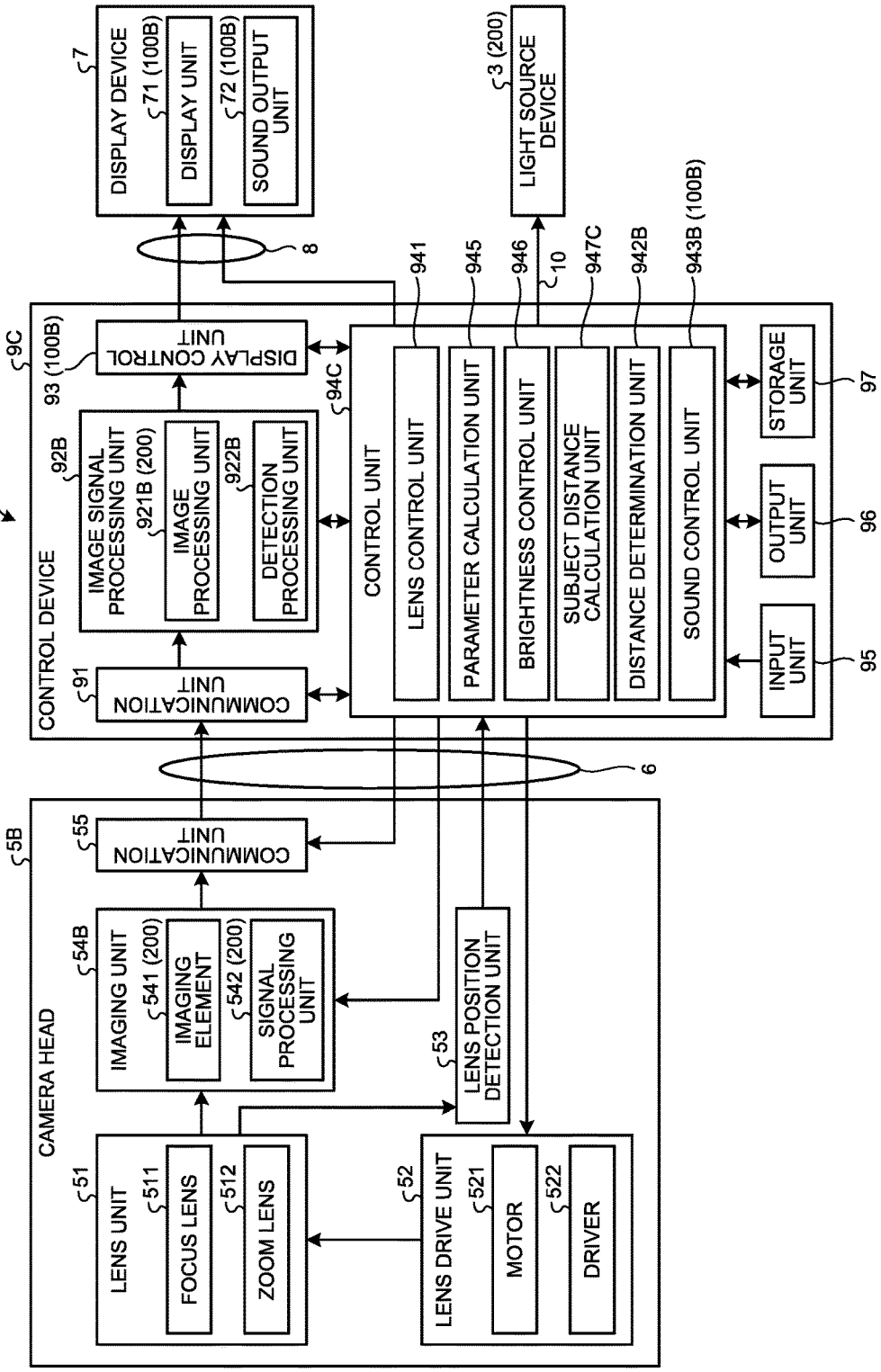
FIG. 17 is a diagram illustrating a schematic configuration of an endoscope device according to a fourth embodiment.
Figure 18:
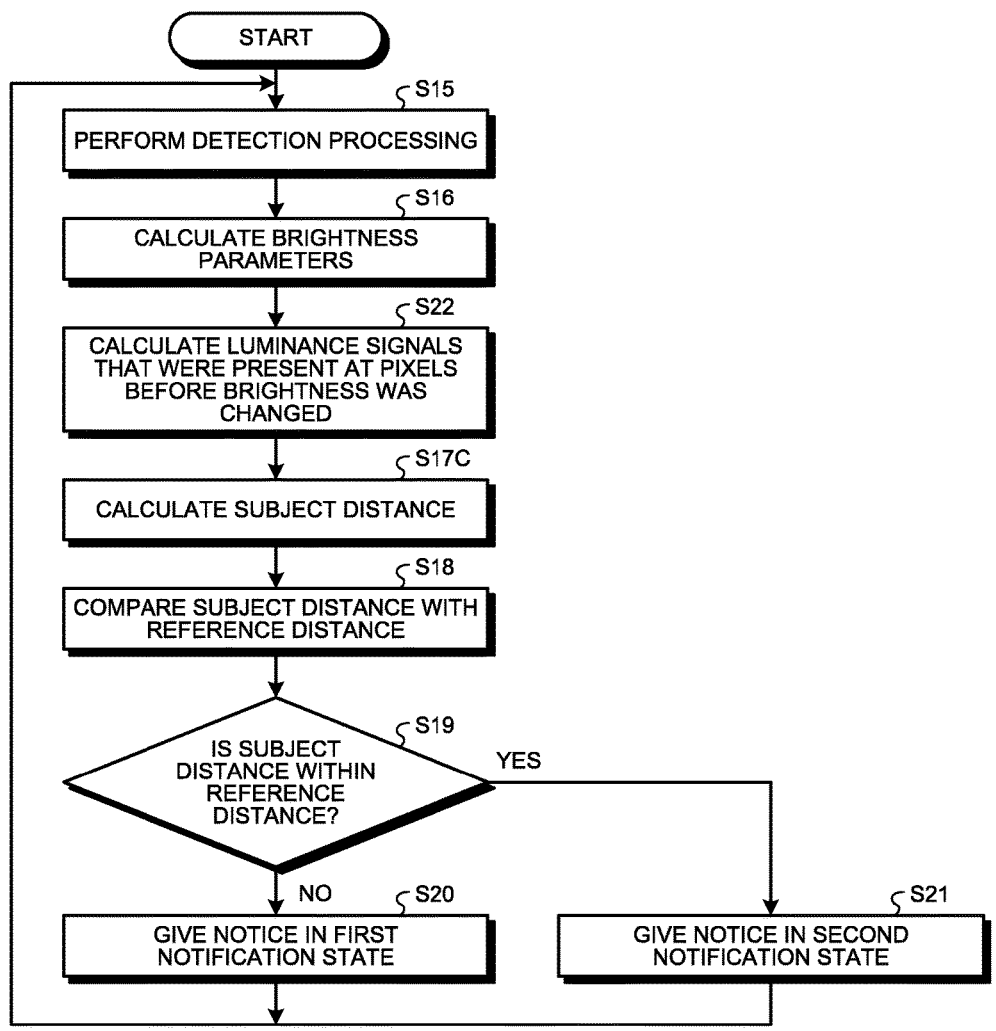
FIG. 18 is a flowchart illustrating operation of the endoscope device.

FIG. 17 is a diagram corresponding to FIG. 14, and illustrates a schematic configuration of an endoscope device 1C according to the fourth embodiment. FIG. 18 is a flowchart illustrating operation of the endoscope device 1C.

As illustrated in FIG. 17, the endoscope device 1C (a control device 9C (a control unit 94C)) according to the fourth embodiment is different from the endoscope device 1B of the third embodiment described above in that a subject distance calculation unit 947C that calculates the subject distance DS by a method different from the method used by the subject distance calculation unit 947 is adopted instead of the subject distance calculation unit 947.

Functions of the subject distance calculation unit 947C will be described below with reference to FIG. 18.

As illustrated in FIG. 18, operation of the endoscope device 1C according to the fourth embodiment is different from the operation of the endoscope device 1B of the third embodiment described above (FIG. 16) in that Step S22 is added and Step S17C is adopted instead of Step S17. Therefore, Steps S22 and S17C will be described below.

Step S22 is performed after Step S16.

Specifically, at Step S22, the subject distance calculation unit 947C acquires luminance signals (Y signals) among image signals (Y, $C_B/C_R$ signals) processed by the image processing unit 921B. The luminance signals (Y signals) are luminance signals (Y signals) obtained after the brightness change unit 200 changed the brightness to the reference brightness according to the brightness parameters calculated at Step S16. The subject distance calculation unit 947C calculates luminance signals (Y signals) that were present before the brightness change unit 200 changed the brightness to the reference brightness, based on the brightness parameters calculated at Step S16 and the luminance signals (Y signals) acquired from the image processing unit 921B.

Step S17C is performed after Step S22.

Specifically, at Step S17C, based on the luminance signal (Y signal) at each of pixels of the same area as the detection area that is subjected to the detection processing among the luminance signals (Y signals) that were calculated at Step S22 and that were present before the brightness was changed to the reference brightness, the subject distance calculation unit 947C calculates a luminance average value of an image in this area. The subject distance calculation unit 947C converts the calculated luminance average value to the subject distance DS using a predetermined relational expression or LUT.

After Step S17C, the endoscope device 1C proceeds to Step S18.

Even when the subject distance DS is calculated as in the fourth embodiment described above, it is possible to achieve the same effects as those of the third embodiment described above.

Fifth Embodiment

Next, a fifth embodiment will be described.

In the following description, the same components as those of the first embodiment described above are denoted by the same reference signs, and detailed explanation thereof will be omitted or simplified.

Figure 19:
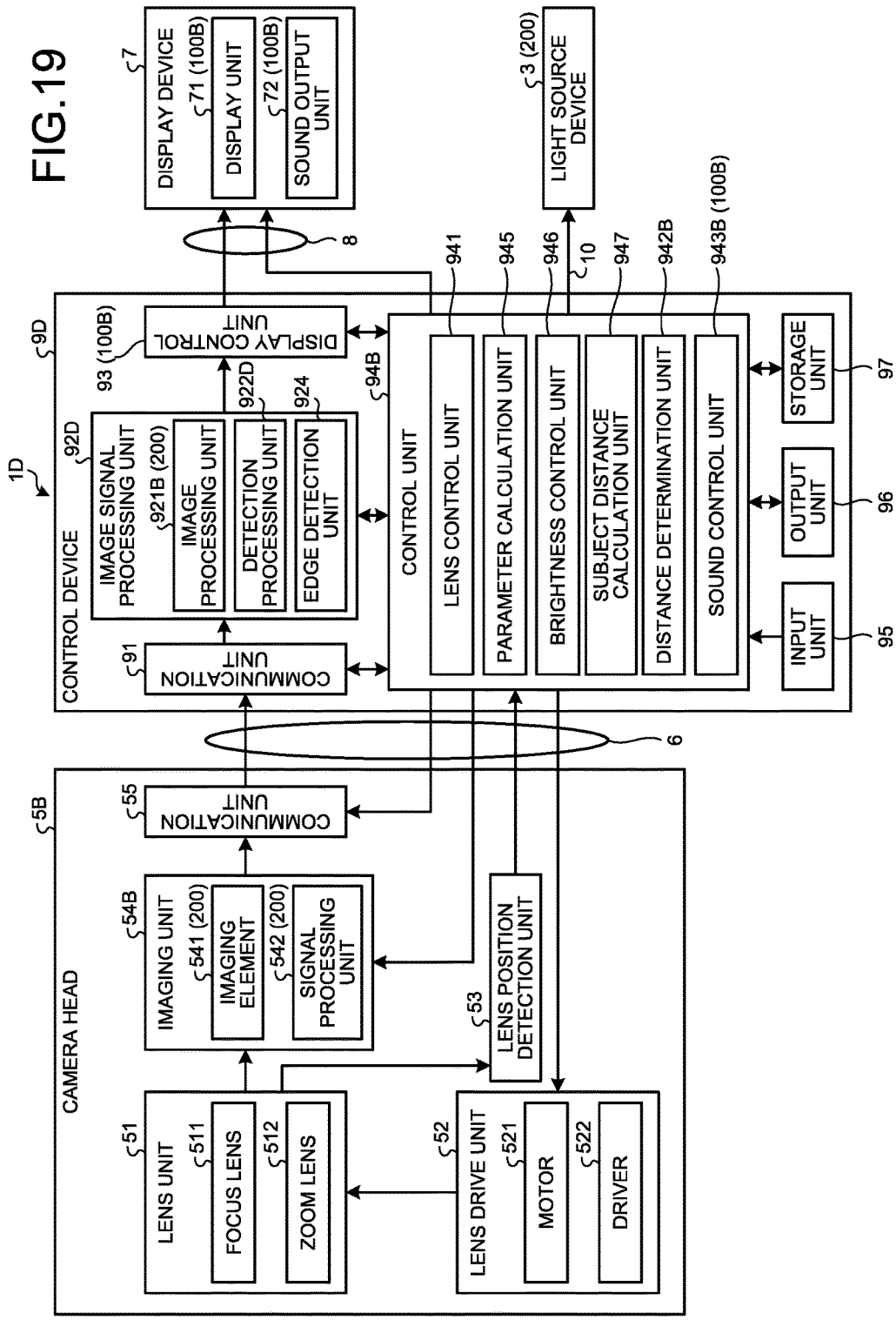
FIG. 19 is a diagram illustrating a schematic configuration of an endoscope device according to a fifth embodiment.
Figure 20:
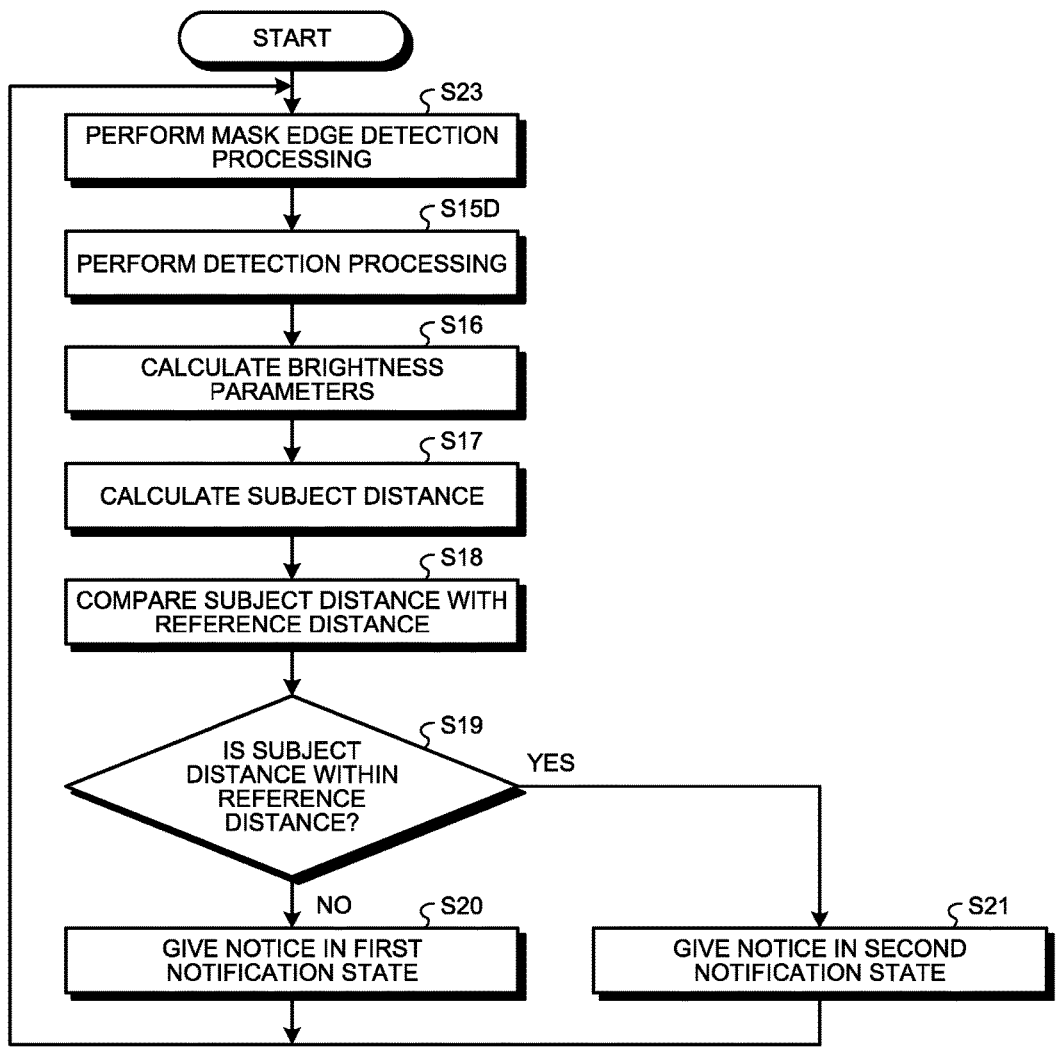
FIG. 20 is a flowchart illustrating operation of the endoscope device.

FIG. 19 is a diagram corresponding to FIG. 14, and illustrates a schematic configuration of an endoscope device 1D according to the fifth embodiment. FIG. 20 is a flowchart illustrating operation of the endoscope device 1D.

As illustrated in FIG. 19, the endoscope device 1D (a control device 9D) according to the fifth embodiment includes an image signal processing unit 92D that has different functions as those of the image signal processing unit 92B in the endoscope device 1B of the third embodiment described above.

As illustrated in FIG. 19, the image signal processing unit 92D is configured by adding an edge detection unit 924 that performs mask edge detection processing to the image signal processing unit 92B of the third embodiment described above, and including a detection processing unit 922D that uses a different detection area as that of the detection processing unit 922B.

Functions of the edge detection unit 924 and the detection processing unit 922D will be described below with reference to FIG. 20.

As illustrated in FIG. 20, operation of the endoscope device 1D according to the fifth embodiment is different from the operation of the endoscope device 1B of the third embodiment described above (FIG. 16) in that Step S23 is added and Step S15D is adopted instead of Step S15. Therefore, Steps S23 and S15D will be described below.

At Step S23, the edge detection unit 924 performs mask edge detection processing.

Figure 21:
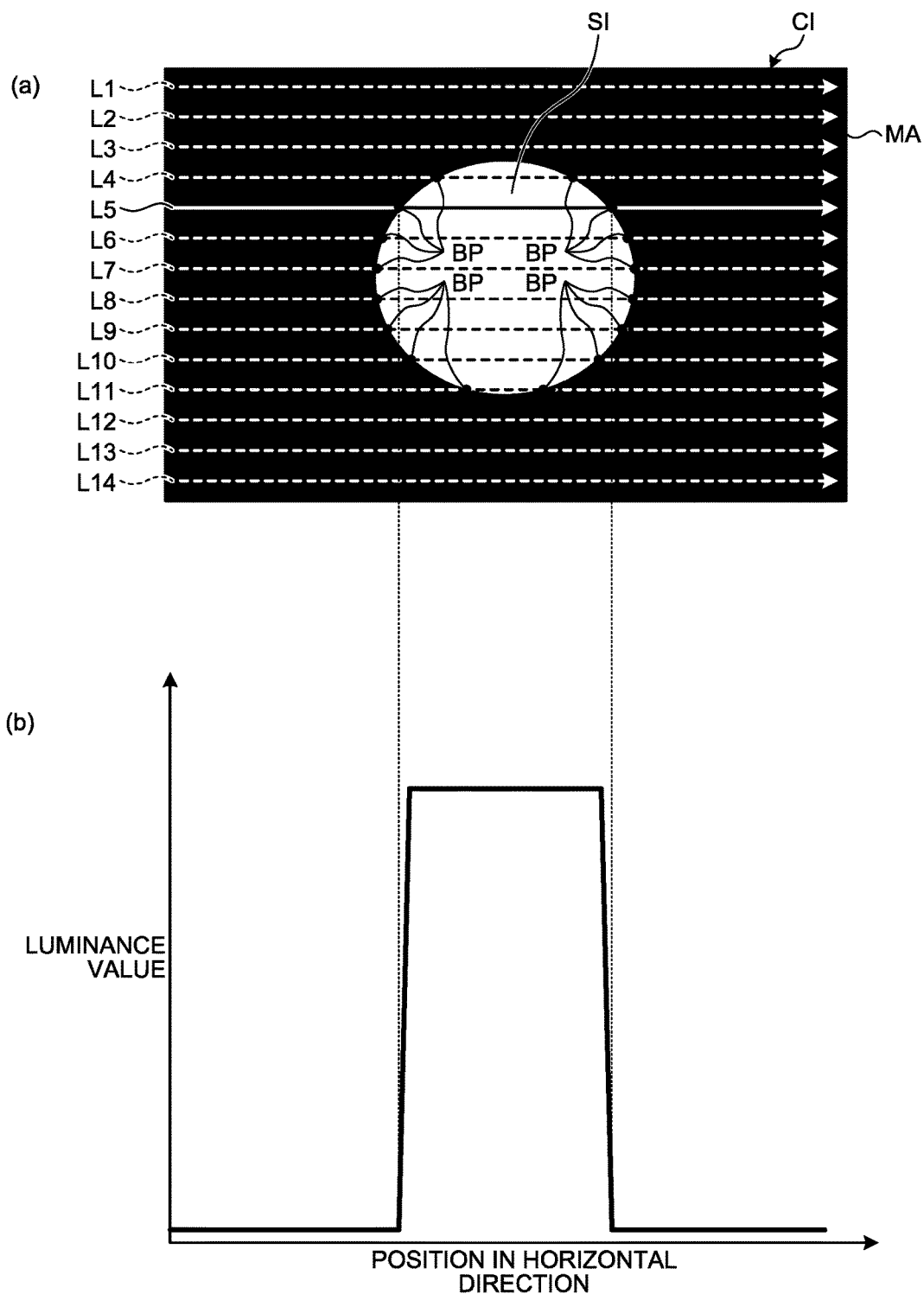
FIG. 21 is a diagram for explaining mask edge detection processing.

FIG. 21 is a diagram for explaining the mask edge detection processing. Specifically, a part (a) of FIG. 21 is a diagram illustrating an example of the captured image CI. A part (b) of FIG. 21 is a diagram illustrating a distribution of luminance values on a horizontal line L5 in the captured image CI illustrated in the part (a) of FIG. 21.

The light (subject image) reflected in a living body and condensed by the insertion unit 2 has a substantially circular cross section. Therefore, as illustrated in the part (a) of FIG. 21, the subject image SI inside the captured image CI has a substantially circular shape. That is, the captured image CI includes the subject image SI and a mask area MA (black portion in the part (a) of FIG. 21) other than the subject image SI.

The edge detection unit 924 detects boundary points BP (The part (a) of FIG. 21) between the subject image SI and the mask area MA by performing the mask edge detection processing at Step S23.

Specifically, as illustrated in the part (a) of FIG. 21, the edge detection unit 924 acquires the luminance signals (Y signal) among the image signals (Y, $C_B/C_R$ signals) processed by the image processing unit 921B. The edge detection unit 924 detects a distribution of luminance values on each of a plurality of horizontal lines L1 to L14 (14 lines in the fifth embodiment) in the captured image CI based on the luminance signals (Y signals). In the captured image CI, the area of the subject image SI has higher luminance values than the mask area MA. That is, as illustrated in the part (b) of FIG. 21, the luminance distribution of the horizontal line L5 indicates that the luminance values between the two boundary points BP of the subject image SI and the mask area MA are high and the luminance values in other portions are low, for example. Therefore, the edge detection unit 924 can recognize the plurality of boundary points BP between the subject image SI and the mask area MA by detecting each of the distributions of the luminance values on the plurality of horizontal lines L1 to L14. Further, the edge detection unit 924 recognizes the area of the subject image SI enclosed by the plurality of boundary points BP, based on the plurality of recognized boundary points BP.

Step S15D is performed after Step S23.

Specifically, at Step S15D, the detection processing unit 922D acquires the luminance signals (Y signals) among the image signals (Y, $C_B/C_R$ signals) processed by the image processing unit 921B. The detection processing unit 922D determines the area of the subject image SI enclosed by the plurality of boundary points BP detected at Step S23 as a detection area. The detection processing unit 922D detects contrast or frequency components of an image in the detection area and also detects a luminance average value of the image in the detection area, based on the luminance signal (Y signal) at each of pixels in the detection area among the acquired luminance signals (Y signals). The detection processing unit 922D outputs detection information (the contrast or frequency components, and the luminance average value) obtained by the detection to the control unit 94B.

After Step S15D, the endoscope device 1D proceeds to Step S16.

According to the fifth embodiment described above, it is possible to achieve the same effects as those of the third embodiment described above, and further achieve the effects as described below.

The endoscope device 1D according to the fifth embodiment detects the plurality of boundary points BP between the subject image SI and the mask area MA by the mask edge detection processing, and performs the detection processing using the area of the subject image SI enclosed by the plurality of boundary points BP as the detection area.

Therefore, it is possible to perform the detection processing using the maximum wide detection area (substantially the whole area of the subject image SI) except for the mask area MA. That is, it is possible to highly accurately perform processing (for example, AF processing, brightness parameter calculation processing, or the like) that is based on the detection information obtained by the detection processing.

Sixth Embodiment

Next, a sixth embodiment will be described.

In the following description, the same components as those of the third embodiment described above are denoted by the same reference signs, and detailed explanation thereof will be omitted or simplified.

Figure 22:
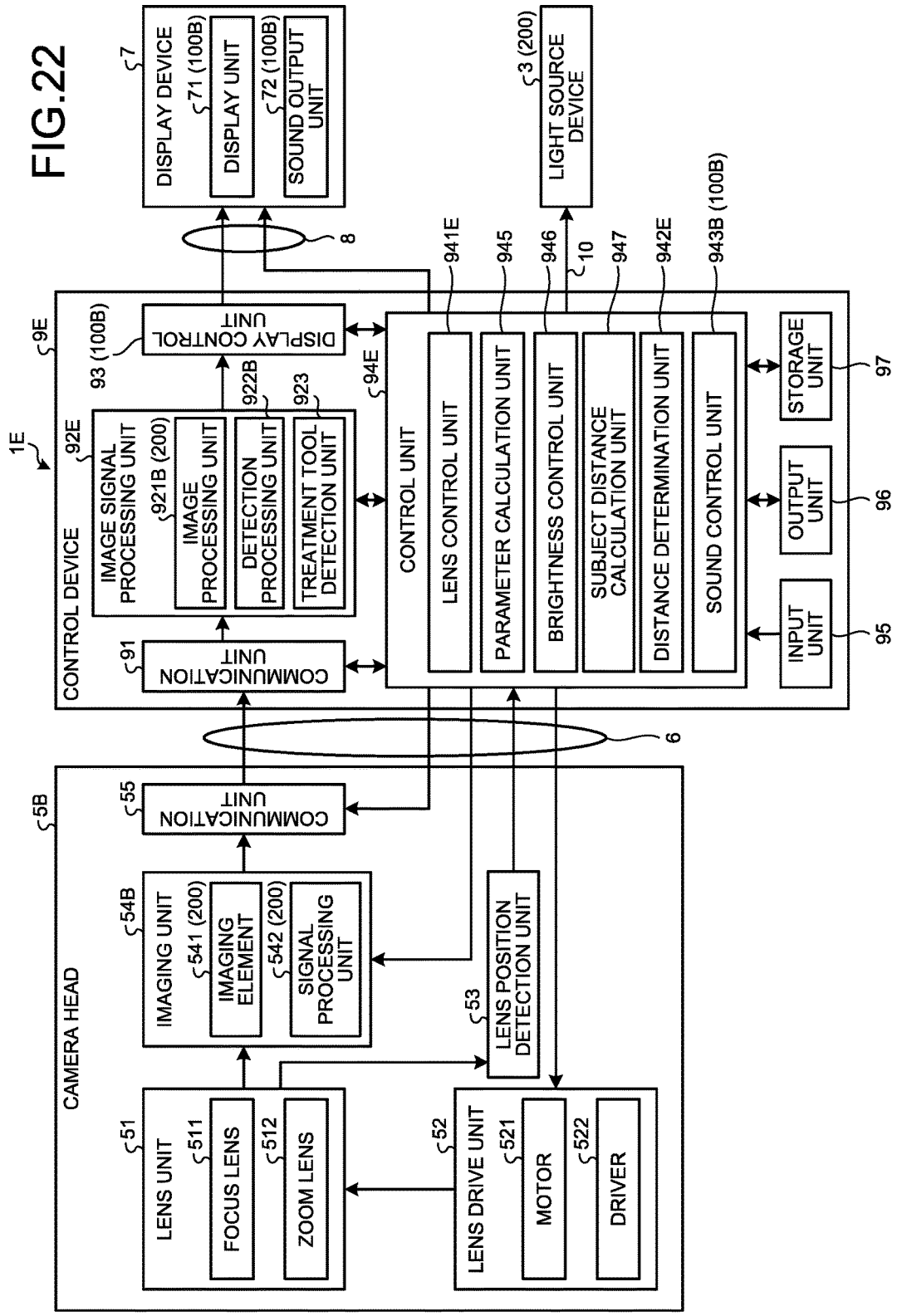
FIG. 22 is a diagram illustrating a schematic configuration of an endoscope device according to a sixth embodiment.
Figure 23:
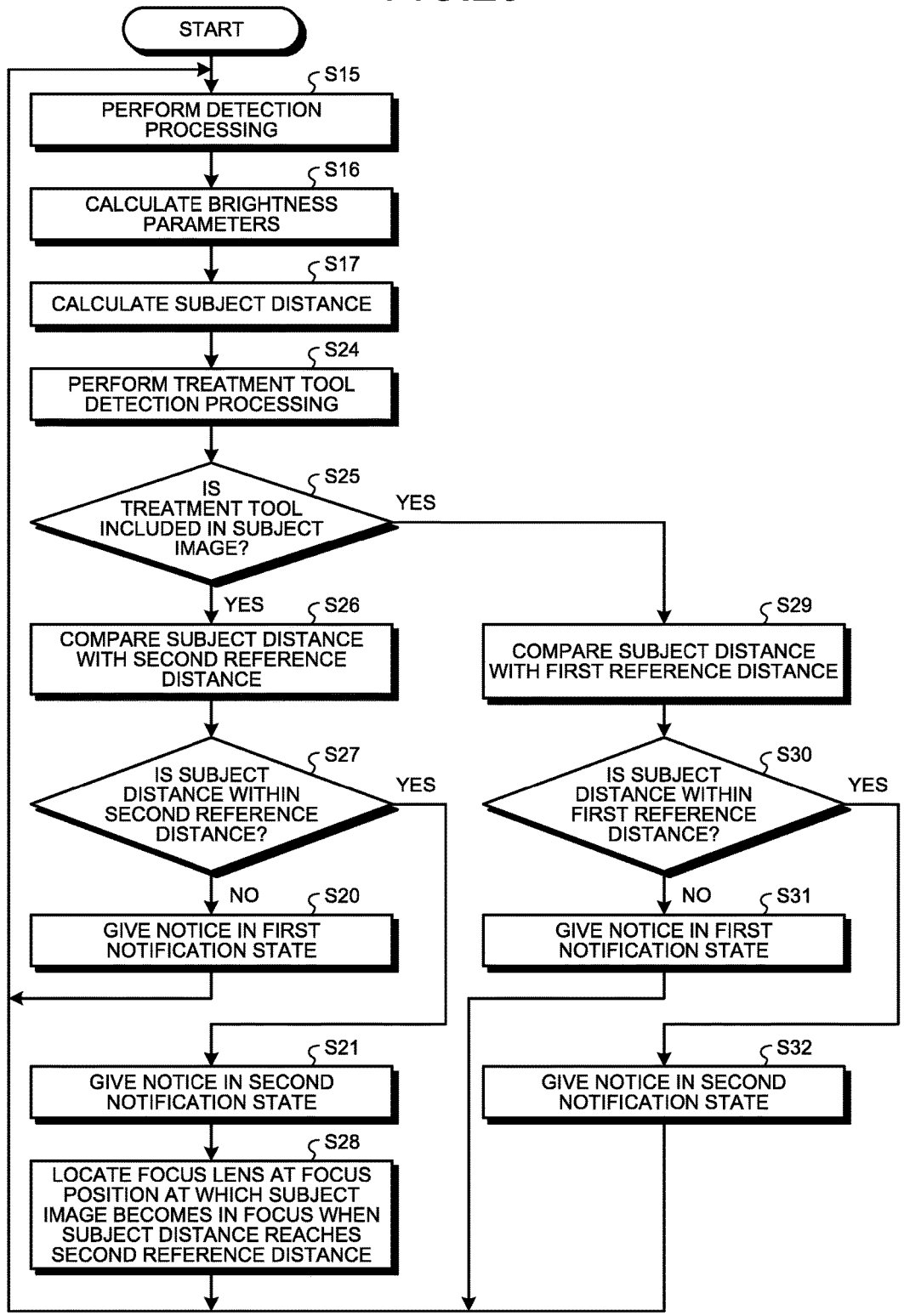
FIG. 23 is a flowchart illustrating operation of the endoscope device.

FIG. 22 is a diagram corresponding to FIG. 14, and illustrates a schematic configuration of an endoscope device 1E according to the sixth embodiment. FIG. 23 is a flowchart illustrating operation of the endoscope device 1E.

As illustrated in FIG. 22, the endoscope device 1E (a control device 9E) according to the sixth embodiment includes an image signal processing unit 92E that is configured by adding the treatment tool detection unit 923 described in the first embodiment to the image signal processing unit 92B included in the endoscope device 1B of the third embodiment described above. The endoscope device 1E (a control unit 94E) further includes a lens control unit 941E and a distance determination unit 942E that are configured by adding new functions to the lens control unit 941 and the distance determination unit 942B.

Functions of the lens control unit 941E and the distance determination unit 942E will be described below with reference to FIG. 23.

As illustrated in FIG. 23, operation of the endoscope device 1E according to the sixth embodiment is different from the operation of the endoscope device 1B of the third embodiment described above (FIG. 16) in that Steps S18 and S19 are omitted and Steps S24 to S32 are added. Therefore, Steps S24 to S32 will be described below.

Steps S24 and S25 are performed after Step S17.

Specifically, the treatment tool detection unit 923 performs the treatment tool detection processing, similarly to the processing at Steps S2 and S3 of the first embodiment described above (Step S24), and determines whether the treatment tool Tt is included in the subject image SI inside the captured image CI (Step S25). If it is determined that the treatment tool Tt is not included in the subject image SI inside the captured image CI (FIG. 3), the treatment tool detection unit 923 outputs a detection signal, which indicates that the treatment tool Tt is not used, to the control unit 94E. In contrast, if it is determined that the treatment tool Tt is included in the subject image SI inside the captured image CI (FIG. 4), the treatment tool detection unit 923 outputs a detection signal, which indicates that the treatment tool Tt is used, to the control unit 94B.

If it is determined that the treatment tool Tt is included (Yes at Step S25), the distance determination unit 942E compares the subject distance DS calculated at Step S17 with the second reference distance D2 (Step S26), and determines whether the subject distance DS is within the second reference distance D2 (Step S27).

In the sixth embodiment, the reference distance described in the third embodiment above is segmented into two reference distances such as the first reference distance D1 and the second reference distance D2, similarly to the first embodiment described above. Further, in the sixth embodiment, the first reference distance D1 is set to "10", and the second reference distance D2 is set to "20" that is longer than the first reference distance (the range of the subject distance DS is from "0" to "100").

If it is determined that the subject distance DS exceeds the second reference distance D2 (No at Step S27), the endoscope device 1E proceeds to Step S20.

In contrast, if it is determined that the subject distance DS is within the second reference distance D2 (Yes at Step S27), the endoscope device 1E proceeds to Step S21.

After Step S21, the lens control unit 941E locates the focus lens 511 at a focus position at which the subject image SI becomes in focus when the subject distance DS reaches the second reference distance D2 (Step S28). Thereafter, the endoscope device 1E returns to Step S15.

At Step S25, if it is determined that the treatment tool Tt is not included (No at Step S25), the distance determination unit 942E compares the subject distance DS calculated at Step S17 with the first reference distance D1 (Step S29), and determines whether the subject distance DS is within the first reference distance D1 (Step S30).

If it is determined that the subject distance DS exceeds the first reference distance D1 (No at Step S30), the distance information notification unit 100B gives a notice of the distance information on the subject distance DS in the first notification state (Step S31). Thereafter, the endoscope device 1E returns to Step S15.

For example, at Step S31, the distance information notification unit 100B gives a notice of the distance information on the subject distance DS in the first notification state as illustrated in FIG. 11. In the sixth embodiment, the level bar LB illustrated in FIG. 11 is a scale corresponding to the range of the subject distance DS ("0" to "100"). Further, the slider SL illustrated in FIG. 11 indicates a position on the level bar LB corresponding to the subject distance DS calculated at Step S17. Furthermore, the first threshold mark SM1 illustrated in FIG. 11 indicates the first reference distance ("10").

In contrast, if it is determined that the subject distance DS is within the first reference distance D1 (Yes at Step S30), the distance information notification unit 100B gives a notice of the distance information on the subject distance DS in the second notification state that is different from the first notification state used at Step S31 (Step S32). Thereafter, the endoscope device 1E returns to Step S15.

For example, at Step S32, the distance information notification unit 100B gives a notice of the distance information on the subject distance DS in the second notification state as illustrated in FIG. 12. In the sixth embodiment, the level bar LB illustrated in FIG. 12 is a scale corresponding to the range of the subject distance DS ("0" to "100"). Further, the slider SL illustrated in FIG. 12 indicates a position on the level bar LB corresponding to the subject distance DS calculated at Step S17. Furthermore, the first threshold mark SM1 illustrated in FIG. 12 indicates the first reference distance ("10"). Moreover, as illustrated in FIG. 12, the distance information notification unit 100B (the sound control unit 943B) outputs an alarm sound (beep sound in the example in FIG. 12) from the display device 7 (the sound output unit 72).

That is, the distance information notification unit 100B gives a notice of the distance information (the subject distance level meter LM and the alarm sound illustrated in FIG. 11 and FIG. 12) in different notification states (the first and second notification states) between when the distance determination unit 942E determines that the subject distance DS exceeds the first reference distance D1 and when the distance determination unit 942E determines that the subject distance DS is within the first reference distance D1.

According to the sixth embodiment described above, it is possible to achieve the same effects as those of the third embodiment described above, and further achieve the effects as described below.

The endoscope device 1E according to the sixth embodiment determines whether the subject distance DS is within the first reference distance D1 when the treatment tool Tt is not used, and determines whether the subject distance DS is within the second reference distance D2 when the treatment tool Tt is used.

Therefore, it is possible to urge a doctor or the like to keep the distal end of the insertion unit 2 away from the subject Su such that the subject distance DS becomes longer than the second reference distance D2 only when the treatment tool Tt is in the used state and the distal end of the insertion unit 2 is likely to get dirty by the mist Mi. That is, when the treatment tool Tt is not used and the distal end of the insertion unit 2 can hardly get dirty by the mist Mi, the doctor or the like is not urged as described above, but can set the subject distance DS to the preferred subject distance DS that may be shorter than the second reference distance D2.

In particular, in the treatment tool detection processing, the non-used state and the used state of the treatment tool Tt are detected by image processing (pattern matching). That is, the non-used state and the used state of the treatment tool Tt are automatically detected by the endoscope device 1. Therefore, as compared to a configuration in which an operation button is provided in the endoscope device 1 and the endoscope device 1 detects the used state of the treatment tool Tt in accordance with an operation on the operation button performed by a doctor or the like for example, it is not necessary to urge the doctor or the like to perform this operation, and therefore, it is possible to improve usability.

Further, when the subject distance DS is within the second reference distance D2, the endoscope device 1E according to the sixth embodiment locates the focus lens 511 at the second threshold at which the subject image SI becomes in focus at the second reference distance D2.

Therefore, a doctor or the like can easily locate the distal end of the insertion unit 2 at a position at which the distal end is less likely to get dirty by the mist Mi, by moving the distal end of the insertion unit 2 away from the subject Su until the subject image SI becomes in focus while checking the display image DI displayed on the display device 7 (the display unit 71).

Other Embodiments

While the embodiments are described above, the present disclosure is not to be limited only by the first to sixth embodiments described above.

In the first to sixth embodiments described above, at least a part of the components (the lens unit 51, the lens drive unit 52, the lens position detection unit 53, and the imaging units 54 and 54B) mounted in the camera heads 5, 5A, and 5B may be mounted on a distal end inside the insertion unit 2.

Further, the insertion unit 2 is not limited to a rigid endoscope, but a flexible endoscope may be adopted instead.

In the first to sixth embodiments described above, at least a part of the functions of the control units 94, 94A to 94C, and 94E may be provided in a unit (the camera heads 5, 5A, and 5B, the connectors CN1 and CN2, or the like) outside the control devices 9 and 9A to 9E.

In the first to sixth embodiments described above, the arrangement position of the sound output unit 72 is not limited to the display device 7, but the control devices 9 and 9A to 9E or the camera heads 5, 5A, and 5B may be adopted instead.

In the first to sixth embodiments described above, the first and second notification states (FIG. 9 to FIG. 12) are described by way of example only, and it is possible to display the distance information in a display state different from the subject distance level meter LM or output the display information in a sound output state different from an alarm sound, as long as different notification states are adopted.

In the first to sixth embodiments described above, the endoscope devices 1 and 1A to 1E may be used in the industrial field and adopted as an endoscope device that observes inside a subject, such as a mechanical structure.

In the first to sixth embodiments described above, the zoom lens 512 is adopted as the image enlargement unit, but the present disclosure is not limited thereto. The image processing units 921 and 921B may be configured to have electronic zoom functions for enlarging a part of the subject image SI, and may be adopted as the image enlargement unit.

In the first to sixth embodiments described above, the focus lens 511 and the zoom lens 512 are electrically moved by the lens drive unit 52, but the present disclosure is not limited thereto. For example, it may be possible to adopt a configuration including a focus ring and a zoom lens, and mechanically move the focus lens 511 and the zoom lens 512 in accordance with rotation operation of the focus ring and the zoom ring.

In the first and second embodiments described above, the two reference distances such as the first and second reference distances D1 and D2 are adopted as the reference distances (two thresholds such as the first and second thresholds are adopted), but the present discloser is not limited thereto. It may be possible to adopt only one of the two reference distances.

In the third to sixth embodiments described above, the brightness change unit 200 includes the four components such as the imaging element 541, the signal processing unit 542, the image processing unit 921B, and the light source device 3, but is not limited thereto, and may be configured using at least any of the four components or may additionally include other components. The same applies to the brightness parameters.

In the third to sixth embodiments described above, the parameter calculation unit 945 is configured to automatically calculate the brightness parameters based on the detection information (luminance average value), but is not limited thereto. For example, it may be possible to provide brightness parameters at a plurality of levels in advance, and allow a doctor or the like to select any of the brightness parameters at the plurality of levels through operation on the input unit 95 or the like. In this case, the brightness control unit 946 controls operation of the brightness change unit 200 based on the brightness parameter selected by the doctor or the like.

In the first, second, and sixth embodiments described above, the treatment tool detection processing is not limited to the image processing (pattern matching) described in the first, second, and sixth embodiments, but may be configured to detect the used state and the non-used state of the treatment tool Tt in accordance with operation on an operation button that is for outputting an operation signal indicating that the treatment tool Tt is used.

Various other embodiments may be made by appropriate combination of the constituent elements disclosed in the first to sixth embodiments. Specifically, the first to sixth embodiments include embodiments according to Notes 1 to 12 described below.

1. An endoscope device comprising:
an insertion unit that is inserted into a subject and captures a subject image inside the subject from a distal end thereof;
an imaging unit that captures the subject image;
a lens unit that includes a focus lens configured to move along an optical axis to adjust a focal point, and forms the subject image captured by the insertion unit onto the imaging unit;
a lens position detection unit that detects a lens position of the focus lens;
a distance information notification unit that gives a notice of distance information on a subject distance based on the lens position, the subject distance being a distance between the distal end of the insertion unit and the subject; and
a distance determination unit that determines whether the subject distance is within a reference distance based on the lens position, wherein
the distance information notification unit gives the notice of the distance information in different notification states between when the distance determination unit determines that the subject distance exceeds the reference distance and when the distance determination unit determines that the subject distance is within the reference distance.

2. The endoscope device according to Note 1, wherein the lens position detection unit is a position sensor that detects the lens position.

3. The endoscope device according to Note 1, further comprising:
a lens drive unit that moves the focus lens; and
a lens control unit that controls operation of the lens drive unit, wherein
the lens position detection unit detects the lens position based on a control value that is output from the lens control unit to the lens drive unit when the lens control unit operates the lens drive unit.

4. The endoscope device according to Note 1, wherein
the distance information notification unit includes:
a display unit that displays the distance information; and
a display control unit that controls operation of the display unit, and
the display control unit displays the distance information on the display unit in different display states between when the distance determination unit determines that the subject distance exceeds the reference distance and when the distance determination unit determines that the subject distance is within the reference distance.

5. The endoscope device according to Note 1, wherein
the distance information notification unit includes:
a sound output unit that outputs the distance information as sound; and
a sound control unit that controls operation of the sound output unit, and
the sound control unit outputs the distance information as sound from the sound output unit in different output states between when the distance determination unit determines that the subject distance exceeds the reference distance and when the distance determination unit determines that the subject distance is within the reference distance.

6. An endoscope device comprising:
an insertion unit that is inserted into a subject and captures a subject image inside the subject from a distal end thereof;
an imaging unit that captures the subject image;
a brightness change unit that changes brightness of a captured image that is obtained by imaging performed by the imaging unit, in accordance with a brightness parameter for changing the brightness of the captured image;
a subject distance calculation unit that calculates a subject distance based on the brightness parameter, the subject distance being a distance between the distal end of the insertion unit and the subject; and
a distance information notification unit that gives a notice of distance information on the subject distance.

7. The endoscope device according to Note 6, further comprising:
a distance determination unit that determines whether the subject distance is within a reference distance, wherein
the distance information notification unit gives the notice of the distance information in different notification states between when the distance determination unit determines that the subject distance exceeds the reference distance and when the distance determination unit determines that the subject distance is within the reference distance.

8. The endoscope device according to Note 7, further comprising:
a treatment tool detection unit that detects a used state of a treatment tool inserted into the subject, wherein
the reference distance includes a first reference distance and a second reference distance that is longer than the first reference distance, and
the distance determination unit uses the first reference distance as the reference distance when the treatment tool detection unit has not detected the used state of the treatment tool, and uses the second reference distance as the reference distance when the treatment tool detection unit has detected the used state of the treatment tool.

9. The endoscope device according to Note 8, wherein
the treatment tool detection unit detects the used state by determining whether the treatment tool is included in the subject image inside the captured image based on the captured image, and
the distance determination unit uses the first reference distance as the reference distance when the treatment tool detection unit determines that the treatment tool is not included in the subject image inside the captured image, and uses the second reference distance as the reference distance when the treatment tool detection unit determines that the treatment tool is included in the subject image inside the captured image.

10. The endoscope device according to Note 7, further comprising:
a lens unit that includes a focus lens configured to move along an optical axis to adjust a focal point, and forms the subject image captured by the insertion unit onto the imaging unit;
a lens drive unit that moves the focus lens; and
a lens control unit that controls operation of the lens drive unit, wherein
when the distance determination unit determines that the subject distance is within the reference distance, the lens control unit operates the lens drive unit and moves the focus lens to a lens position at which the subject image becomes in focus when the subject distance reaches the reference distance.

11. The endoscope device according to Note 6, wherein the distance information notification unit includes:
a display unit that displays the distance information; and
a display control unit that controls operation of the display unit.

12. The endoscope device according to Note 6, wherein the distance information notification unit includes:
a sound output unit that outputs the distance information as sound; and
a sound control unit that controls operation of the sound output unit.

It should be understood that various effects and modifications may be easily conceived by those skilled in the art. Accordingly, broader modes for carrying out the present disclosure may occur, which are not limited by specific details and representative embodiments illustrated and described herein. Thus, various changes may occur insofar as they are within the sprit and scope of a comprehensive concept of the technology defined by the appended claims or equivalents thereof.

What is claimed is:

1. An endoscope system comprising:
an insertion structure configured to be inserted into a subject and capture a subject image inside the subject from a distal end portion of the insertion structure;
an imaging element configured to capture the subject image; and circuitry configured to
acquire distance information between the distal end portion of the insertion structure and the subject,
determine whether a subject distance is within a reference distance based on the distance information, and
give a notice of the distance information based on the determination made by the circuitry regarding whether the subject distance is within the reference distance, wherein the distance information notification includes the notice of the distance information in different notification states when the subject distance exceeds the reference distance and when the subject distance is within the reference distance.

2. The endoscope system according to claim 1 further comprising:
a treatment tool detector configured to detect a used state of a treatment tool inserted in the subject, wherein
the reference distance includes a first reference distance and a second reference distance that is longer than the first reference distance, and
the circuitry is further configured to use the first reference distance as the reference distance when the treatment tool detector has not detected the used state of the treatment tool, and uses the second reference distance as the reference distance when the treatment tool detector has detected the used state of the treatment tool.

3. The endoscope system according to claim 2, wherein
the treatment tool detector detects the used state by determining whether the treatment tool is included in the subject image inside the captured image based on a captured image that is captured by the imaging element, and
the circuitry is further configured to use the first reference distance as the reference distance when the treatment tool detector determines that the treatment tool is not included in the subject image inside the captured image, and uses the second reference distance as the reference distance when the treatment tool detector determines that the treatment tool is included in the subject image inside the captured image.

4. The endoscope system according to claim 1, further comprising:
a lens assembly including a focus lens configured to move along an optical axis to adjust a focal point, and configured to form the subject image captured by the insertion structure onto the imaging element, wherein
the circuitry is further configured to detect a lens position of the focus lens, and give a notice of distance information on the subject distance based on the lens position.

5. The endoscope system according to claim 4, further comprising:
a lens drive assembly configured to move the focus lens; and
a lens controller configured to control operation of the lens drive assembly, wherein
when the circuitry determines that the subject distance is within the reference distance, the lens controller operates the lens drive assembly and moves the focus lens to a lens position at which the subject image becomes in focus when the subject distance reaches the reference distance.

6. The endoscope system according to claim 1, wherein:
the circuitry is further configured to change brightness of a captured image that is obtained by imaging performed by the imaging element, in accordance with a brightness parameter to change the brightness of the captured image, and
calculate the subject distance based on the brightness parameter.

7. The endoscope system according to claim 6, wherein the imaging element includes a plurality of pixels, and
the circuitry includes the imaging element, and changes the brightness of the captured image by changing exposure times of the pixels, the exposure times serving as the brightness parameter.

8. The endoscope system according to claim 6, wherein the imaging element includes a plurality of pixels, and is configured to capture the subject image and output an analog signal, and includes a signal processor configured to multiply the analog signal by analog gain, wherein
the circuitry includes the signal processor and changes the brightness of the captured image by changing the analog gain that serves as the brightness parameter.

9. The endoscope system according to claim 6, wherein:
the imaging element includes a plurality of pixels, and is configured to capture the subject image and output an analog signal, and includes a signal processor configured to convert the analog signal to a digital signal, wherein
the circuitry is further configured to multiply the digital signal by digital gain that serves as the brightness parameter, and change the brightness of the captured image by changing the digital gain.

10. The endoscope system according to claim 6, further comprising:
a light source configured to supply, to the insertion structure, light that illuminates a subject from the distal end of the insertion structure, wherein
the circuitry includes the light source, and changes the brightness of the captured image by changing an amount of the light that serves as the brightness parameter.

11. The endoscope system according to claim 6, wherein:
the circuitry is further configured to
calculate the brightness parameter based on a luminance signal at each of pixels of the captured image,
control changes in brightness based on the brightness parameter,
and convert the brightness parameter to a subject distance.

12. The endoscope system according to claim 6, wherein the circuitry calculates, based on a luminance signal at each of pixels of the captured image and the brightness parameter, a luminance signal that was present at each of the pixels of the captured image before the brightness was changed by the circuitry, and calculates the subject distance based on the luminance signal that was present at each of the pixels of the captured image before the brightness was changed.

13. The endoscope system according to claim 6, wherein the captured image includes the subject image and a mask area other than the subject image, and
the
the circuitry is further configured to
detect boundary points between the subject image and the mask area based on the luminance signal at each of the pixels of the captured image,
calculate the brightness parameter based on the luminance signal at each of pixels in an area enclosed by the boundary points in the captured image detected by the edge detection unit, and
control changes in brightness based on the brightness parameter.

14. The endoscope system according to claim 1, wherein the circuitry is further configured to enlarge the subject image included in the captured image obtained by imaging performed by the imaging element.

* * * * *